(12) United States Patent
Guiraldes et al.

(10) Patent No.: US 12,653,131 B2
(45) Date of Patent: Jun. 16, 2026

---

(54) SOYBEAN VARIETY '10020889166'

(71) Applicants:GDM Argentina S.A., Chacabuco (AR); GDM Genética do Brasil S.A., Cambé (BR)

(72) Inventors: Marcos Quiroga Guiraldes, Chacabuco (AR); Ezequiel Eduardo Pozzo San Martin, Chacabuco (AR); Eduardo Irusta, Chacabuco (AR)

(73) Assignee: GDM Argentina S.A., Chacabuco (AR)

( * ) Notice: Subject to any disclaimer, the term of this patent is extended or adjusted under 35 U.S.C. 154(b) by 205 days.

(21) Appl. No.: 18/240,270

(22) Filed: Aug. 30, 2023

(65) Prior Publication Data

US 2024/0074397 A1    Mar. 7, 2024

Related U.S. Application Data

(60) Provisional application No. 63/403,266, filed on Sep. 1, 2022.

(51) Int. Cl.
*A01H 5/10* (2018.01)
*A01H 6/54* (2018.01)

(52) U.S. Cl.
CPC .............. *A01H 6/542* (2018.05); *A01H 5/10* (2013.01)

(58) Field of Classification Search
None
See application file for complete search history.

(56) References Cited

U.S. PATENT DOCUMENTS

| | | | |
|---|---|---|---|
| 6,958,437 | B1 | 10/2005 | Gebhardt et al. |
| 9,232,760 | B2 | 1/2016 | Wooten et al. |
| 9,756,812 | B2 | 9/2017 | Mason |
| 9,894,873 | B1 | 2/2018 | Corbin et al. |
| 10,555,469 | B2 | 2/2020 | Guiraldes et al. |
| 10,798,907 | B2 | 10/2020 | Guiraldes et al. |
| 10,905,072 | B1 | 2/2021 | Wooten et al. |
| 11,382,299 | B2 | 7/2022 | Guiraldes et al. |
| 11,744,212 | B2 | 9/2023 | Pignata et al. |
| 12,193,403 | B2 | 1/2025 | Pignata et al. |
| 12,207,617 | B2 | 1/2025 | Garcia et al. |
| 12,207,618 | B2 | 1/2025 | Garcia et al. |
| 12,336,482 | B2 | 6/2025 | Guiraldes et al. |
| 2009/0019581 | A1 | 1/2009 | Narvel |
| 2018/0213740 | A1 | 8/2018 | Guiraldes et al. |
| 2019/0166786 | A1 | 6/2019 | Guiraldes et al. |
| 2020/0288663 | A1 | 9/2020 | Guiraldes et al. |
| 2021/0100202 | A1* | 4/2021 | Cervantes Martinez et al. ........... A01H 6/54 |
| 2021/0185963 | A1 | 6/2021 | Garcia et al. |
| 2021/0195862 | A1 | 7/2021 | Pignata et al. |
| 2022/0192129 | A1 | 6/2022 | Guiraldes et al. |
| 2022/0295731 | A1 | 9/2022 | Guiraldes et al. |
| 2023/0165210 | A1 | 6/2023 | Guiraldes et al. |
| 2023/0165211 | A1 | 6/2023 | Guiraldes et al. |
| 2023/0172144 | A1 | 6/2023 | Guiraldes et al. |
| 2023/0337617 | A1 | 10/2023 | Garcia et al. |
| 2023/0345899 | A1 | 11/2023 | Pignata et al. |
| 2023/0371455 | A1 | 11/2023 | Garcia et al. |
| 2024/0074395 | A1 | 3/2024 | Guiraldes et al. |
| 2024/0074396 | A1 | 3/2024 | Guiraldes et al. |
| 2024/0130315 | A1 | 4/2024 | Guiraldes et al. |
| 2024/0180115 | A1 | 6/2024 | Guiraldes et al. |
| 2024/0180116 | A1 | 6/2024 | Guiraldes et al. |
| 2024/0180117 | A1 | 6/2024 | Guiraldes et al. |
| 2025/0098615 | A1 | 3/2025 | Schmitz et al. |
| 2025/0098616 | A1 | 3/2025 | Pozzo San Martin et al. |
| 2025/0098617 | A1 | 3/2025 | Pozzo San Martin et al. |
| 2025/0098618 | A1 | 3/2025 | Pignata et al. |
| 2025/0098619 | A1 | 3/2025 | Garcia et al. |
| 2025/0280782 | A1 | 9/2025 | Guiraldes et al. |

OTHER PUBLICATIONS

Ex parte C, 27 U.S.P.Q.2d 1492 (Bd.Pat.App.&Interf.), 1992 WL 515817, Board of Patent Appeals and Interferences (Year: 1992) (Year: 1992).*
Haun et al, The Composition and Origins of Genomic Variation among Individuals of the Soybean Reference Cultivar Williams 82, Plant Physiology, Feb. 2011, vol. 155, pp. 645-655 (Year:2011) (Year: 2011).*
Grobkinsky, Plant phenomics and the need for physiological phenotyping across scales to narrow the genotype-to-phenotype knowledge gap, Journal of Experimental Botany, vol. 66, No. 18, pp. 5429-5440, 2015 (Year: 2015).*
UPOV, Explanatory Notes On Essentially Derived Varieties Under The 1991 Act of the UPOV Convention (Year:2017) (Year: 2017).*
Mcgowan, Appeal 2019-006060, U.S. Appl. No. 14/996,093 (Year:2020) (Year: 2020).*
USDA, Applying for a Plant Variety Certificate of Protection, www.ams.usda.gov (Year:2023) (Year: 2023).*
Großkinsky et al., (2015). "Plant phenomics and the need for physiological phenotyping across scales to narrow the genotype-to-phenotype knowledge gap," J Exp Bot, 66(18):5429-5440.
Haun et al., (2011). "The Composition and Origins of Genomic Variation among Individuals of the Soybean Reference Cultivar Williams 82," Plant Physiology, 155(2):645-655.
UPOV (2017). "UPOV/EXN/EDV/2: Explanatory Notes on Essentially Derived Varieties Under the 1991 Act of the UPOV Convention," available online at <https://www.upov.int/edocs/expndocs/en/upov_exn_edv.pdf>, 13 pages.
USDA Agricultural Marketing Service (2023). "Applying for a Plant Variety Certificate of Protection," available online at <https://www.ams.usda.gov/services/pvpo/application-help/apply>, 3 pages.
USPTO Ex parte C, 27 USPQ 2d 1492 Board Decision—appeal 92-0393 dated Sep. 28, 1992, 17 pages.
USPTO Ex parte Robert E. McGowen Board Decision—appeal 2019-006060 in U.S. Appl. No. 14/996,093 dated Sep. 9, 2020, 9 pages.
U.S. Appl. No. 19/215,928, filed May 22, 2025 titled "Soybean Variety '20506064'," (Copy not submitted herewith pursuant to the waiver of 37 C.F.R. § 1.98(a)(2)(iii)).
U.S. Appl. No. 18/216,492, filed Jun. 29, 2023 titled "Soybean Variety '20013989'," (Copy not submitted herewith pursuant to the waiver of 37 C.F.R. § 1.98(a)(2)(iii)).

(Continued)

*Primary Examiner* — Amjad Abraham
*Assistant Examiner* — Christina L Meadows
(74) *Attorney, Agent, or Firm* — Morrison & Foerster LLP

(57) ABSTRACT

New soybean variety designated '10020889166' is a soybean variety exhibiting stability and uniformity.

17 Claims, No Drawings

(56)        References Cited

OTHER PUBLICATIONS

U.S. Appl. No. 18/216,535, filed Jun. 29, 2023 titled "Soybean Varieties," (Copy not submitted herewith pursuant to the waiver of 37 C.F.R. § 1.98(a)(2)(iii)).
U.S. Appl. No. 18/220,710, filed Jul. 11, 2023 titled "Soybean Varieties '2984004', '2987416', '2987413', And '2987331'," (Copy not submitted herewith pursuant to the waiver of 37 C.F.R. § 1.98(a)(2)(iii)).
U.S. Appl. No. 18/240,259, filed Aug. 30, 2023 titled "Soybean Varieties '20311965', '3520224', '20273637', '20273641', '21237491', '20272663', '10021388457', '10021387697', '20273650', '21237431', '21237487', '10021387142', And '20272659'," (Copy not submitted herewith pursuant to the waiver of 37 C.F.R. § 1.98(a)(2)(iii)).
U.S. Appl. No. 18/240,264, filed Aug. 30, 2023 titled "Soybean Varieties '2962362', '2968682', '2962338', '2980918', '10020854132', '10020849549', '10020849708', '10020853409', '10020853412', '10020855165', '10020851261', '10021286730', '10020851485', '10021352446', '10020849548', '20593358', And '10021355197'," (Copy not submitted herewith pursuant to the waiver of 37 C.F.R. § 1.98(a)(2)(iii)).
USDA Agricultural Marketing Service (2025). "Application for Plant Variety Protection Certificate," available online at <https://www.ams.usda.gov/sites/default/files/media/PVPOST470ApplicationWithExhibitsAndInstructions.pdf>, 9 pages.

* cited by examiner

SOYBEAN VARIETY '10020889166'

CROSS-REFERENCE TO RELATED APPLICATION

This application claims the benefit of U.S. Provisional Application No. 63/403,266, filed on Sep. 1, 2022, which is hereby incorporated by reference in its entirety.

FIELD OF THE INVENTION

The present invention relates to the field of plant breeding. In particular, this invention relates to new soybean, *Glycine max*, varieties designated '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', and '10021384485'.

BACKGROUND OF THE INVENTION

Soybean (*Glycine max*) is a major grain crop valued for the high levels of oil and protein found in soybean seed. Soybean breeding has resulted in significant improvements in yield potential, stability of yield, adaptation of the species to mechanical harvest, and yield protection through improved disease resistance. Soybean is useful not only as a seed for producing soybean plants, but also has utility as a grain. The grain can be used as a food source for both animals and humans. Soybean is widely used as a source of protein for animal feeds for poultry, swine and cattle. The soybean grain is therefore a commodity. Soybean commodity plant products include, but are not limited to, protein concentrate, protein isolate, soybean hulls, meal, flower, oil and the whole soybean itself. Due to the nature of plant science agriculture, broadly defined as a manipulation of available plant resources to meet the needs of the growing human population, the environment in which plants are grown for agricultural production continuously offers new obstacles to agricultural production. Each new cultivar released to agricultural production is selected for the purpose of increasing yield, resulting from increased disease resistance to prevalent diseases, or from direct or indirect improvement in yield potential or efficiency of production. Development of stable, high-yielding cultivars with superior characteristics is an ongoing goal of soybean breeders.

Accordingly, there is a continuing need to develop new soybean varieties that are stable, high-yielding cultivars, and express superior agronomic characteristics.

BRIEF SUMMARY OF THE INVENTION

In order to meet these needs, the present invention is directed to improved soybean varieties.

One aspect of the present disclosure includes a soybean seed designated as '10020720647'. Some embodiments include a soybean plant produced by growing said seed. In other embodiments, the present disclosure is further directed to plant parts from said plant. In some embodiments, the plant parts of any preceding embodiment include a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the plant parts of any preceding embodiment include a pod. In still other embodiments, the present disclosure is directed to a soybean plant having all the physiological and morphological characteristics of the plant of any of the preceding embodiments. Accordingly, some embodiments include a plant part of the soybean plant of any of the preceding embodiments. In some embodiments, the plant part includes a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the part is a pod.

One aspect of the present disclosure is directed to an F1 hybrid soybean plant having '10020720647' as a parent wherein '10020720647' is grown from the seed of any of the preceding embodiments. Some embodiments include a pollen grain or an ovule of the plant of any of the preceding embodiments. Some embodiments include a tissue culture of the plant of any of the preceding embodiments. Some embodiments include a soybean plant regenerated from said tissue culture, wherein the plant has all of the morphological and physiological characteristics of a soybean plant produced by growing seed designated as '10020720647'. Some aspects of the present disclosure are directed to a method of making soybean seeds, said method including crossing the plant of any of the preceding embodiments with another soybean plant and harvesting seed therefrom. Some aspects of the present disclosure are directed to a method of producing a commodity plant product, including obtaining the plant of any of the preceding embodiments or a part thereof and producing said commodity plant product therefrom. In some embodiments, the commodity plant product is protein concentrate, protein isolate, hulls, meal, flour, or oil. In still other aspects, the present disclosure is directed to a method of making a soybean variety '10020720647', said method including selecting seeds from the cross of one '10020720647' plant with another '10020720647' plant.

In still another embodiment, the present invention is further directed to soybean plants, soybean parts from the soybean plants, and seeds produced therefrom where the soybean plant is isolated by the breeding method of the invention. In another embodiment, the present invention is directed to methods for producing a soybean plant containing in its genetic material one or more transgenes and to the transgenic soybean plant produced by those methods. In another embodiment, the present invention is directed to methods for producing a male sterile soybean plant by introducing a nucleic acid molecule that confers male sterility into a soybean plant produced by growing '10020720647' soybean seed, and to male sterile soybean plants produced by such methods. In another embodiment, the present invention is directed to methods of producing an herbicide resistant soybean plant by introducing a gene conferring herbicide resistance into a soybean plant produced by growing '10020720647' soybean seed, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant soybean plants produced by such methods. In another embodiment, the present invention is directed to methods of producing a pest or insect resistant soybean plan by introducing a gene conferring pest or insect resistance into a soybean plant produced by growing '10020720647' soybean seed, and to pest or insect resistant soybean plants produced by such methods. In another embodiment, the present invention is directed to methods of producing a disease resistant soybean plant by introducing a gene conferring disease resistance into a soybean plant produced by growing '10020720647' soybean seed, and to disease resistant soybean plants produced by such methods. In another embodiment, the present invention is directed to methods of producing a soybean plant with a value-added trait by introducing a gene conferring a value-added trait into a soybean plant produced by growing '10020720647' soybean seed, where the gene encodes a protein selected from a ferritin, a nitrate reductase, and a monellin. Certain embodiments are also directed to soybean plants having a value-added trait produced by such methods.

In another embodiment, the present invention is directed to methods of introducing a desired trait into soybean variety '10020720647', by: (a) crossing a '10020720647' plant with a plant of another soybean variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) back-crossing the selected progeny plants with a '10020720647' plant to produce backcross progeny plants; (d) selecting for backcross progeny plants that have the desired trait and all of the physiological and morphological characteristics of soybean variety '10020720647'; and (e) repeating steps (c) and (d) two or more times in succession to produce selected third or higher backcross progeny plants that comprise the desired trait. Certain embodiments are also directed to soybean plants produced by such methods, where the plants have the desired trait and all of the physiological and morphological characteristics of soybean variety '10020720647'. In certain embodiments, the desired trait is herbicide resistance and the resistance is conferred to an herbicide selected from glyphosate, sulfonylurea, imidazoli-none, dicamba, glufosinate, phenoxy proprionic acid, L-phosphinothricin, cyclohexone, cyclohexanedione, triaz-ine, and benzonitrile. In other embodiments, the desired trait is insect or pest resistance and the insect or pest resistance is conferred by a transgene encoding a *Bacillus thuringiensis* endotoxin. In another embodiment, the present invention provides for single gene converted plants of '10020720647'.

The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring soybean gene or a transgene introduced through genetic engineering techniques.

One aspect of the present disclosure includes a soybean seed designated as '10020889109'. Some embodiments include a soybean plant produced by growing said seed. In other embodiments, the present disclosure is further directed to plant parts from said plant. In some embodiments, the plant parts of any preceding embodiment include a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the plant parts of any preceding embodiment include a pod. In still other embodiments, the present disclosure is directed to a soybean plant having all the physiological and morphological characteristics of the plant of any of the preceding embodiments. Accordingly, some embodiments include a plant part of the soybean plant of any of the preceding embodiments. In some embodiments, the plant part includes a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the part is a pod.

One aspect of the present disclosure is directed to an F1 hybrid soybean plant having '10020889109' as a parent wherein '10020889109' is grown from the seed of any of the preceding embodiments. Some embodiments include a pol-len grain or an ovule of the plant of any of the preceding embodiments. Some embodiments include a tissue culture of the plant of any of the preceding embodiments. Some embodiments include a soybean plant regenerated from said tissue culture, wherein the plant has all of the morphological and physiological characteristics of a soybean plant pro-duced by growing seed designated as '10020889109'. Some aspects of the present disclosure are directed to a method of making soybean seeds, said method including crossing the plant of any of the preceding embodiments with another soybean plant and harvesting seed therefrom. Some aspects of the present disclosure are directed to a method of pro-ducing a commodity plant product, including obtaining the plant of any of the preceding embodiments or a part thereof and producing said commodity plant product therefrom. In some embodiments, the commodity plant product is protein concentrate, protein isolate, hulls, meal, flour, or oil. In still other aspects, the present disclosure is directed to a method of making a soybean variety '10020889109', said method including selecting seeds from the cross of one '10020889109' plant with another '10020889109' plant.

In still another embodiment, the present invention is further directed to soybean plants, soybean parts from the soybean plants, and seeds produced therefrom where the soybean plant is isolated by the breeding method of the invention. In another embodiment, the present invention is directed to methods for producing a soybean plant contain-ing in its genetic material one or more transgenes and to the transgenic soybean plant produced by those methods. In another embodiment, the present invention is directed to methods for producing a male sterile soybean plant by introducing a nucleic acid molecule that confers male ste-rility into a soybean plant produced by growing '10020889109' soybean seed, and to male sterile soybean plants produced by such methods. In another embodiment, the present invention is directed to methods of producing an herbicide resistant soybean plant by introducing a gene conferring herbicide resistance into a soybean plant pro-duced by growing '10020889109' soybean seed, where the gene is selected from glyphosate, sulfonylurea, imidazoli-none, dicamba, glufosinate, phenoxy proprionic acid, L-phosphinothricin, cyclohexone, cyclohexanedione, triaz-ine, and benzonitrile. Certain embodiments are also directed to herbicide resistant soybean plants produced by such methods. In another embodiment, the present invention is directed to methods of producing a pest or insect resistant soybean plan by introducing a gene conferring pest or insect resistance into a soybean plant produced by growing '10020889109' soybean seed, and to pest or insect resistant soybean plants produced by such methods. In another embodiment, the present invention is directed to methods of producing a disease resistant soybean plant by introducing a gene conferring disease resistance into a soybean plant produced by growing '10020889109' soybean seed, and to disease resistant soybean plants produced by such methods. In another embodiment, the present invention is directed to methods of producing a soybean plant with a value-added trait by introducing a gene conferring a value-added trait into a soybean plant produced by growing '10020889109' soybean seed, where the gene encodes a protein selected from a ferritin, a nitrate reductase, and a monellin. Certain embodiments are also directed to soybean plants having a value-added trait produced by such methods.

In another embodiment, the present invention is directed to methods of introducing a desired trait into soybean variety '10020889109', by: (a) crossing a '10020889109' plant with a plant of another soybean variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait: (c) back-crossing the selected progeny plants with a '10020889109' plant to produce backcross progeny plants; (d) selecting for backcross progeny plants that have the desired trait and all of the physiological and morphological characteristics of soybean variety '10020889109'; and (e) repeating steps (c) and (d) two or more times in succession to produce selected third or higher backcross progeny plants that comprise the desired trait. Certain embodiments are also directed to soybean plants produced by such methods, where the plants have the desired trait and all of the physiological and morphological characteristics of soybean variety '10020889109'. In certain embodiments, the desired trait is herbicide resistance and the resistance is conferred to an herbicide selected from glyphosate, sulfonylurea, imidazoli-none, dicamba, glufosinate, phenoxy proprionic acid, L-phosphinothricin, cyclohexone, cyclohexanedione, triaz-ine, and benzonitrile. In other embodiments, the desired trait is insect or pest resistance and the insect or pest resistance is conferred by a transgene encoding a *Bacillus thuringiensis* endotoxin. In another embodiment, the present invention provides for single gene converted plants of '10020889109'.

The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring soybean gene or a transgene introduced through genetic engineering techniques.

One aspect of the present disclosure includes a soybean seed designated as '10020889166', representative sample of seed having been deposited under ATCC Accession Number PTA-127941. Some embodiments include a soybean plant produced by growing said seed. In other embodiments, the present disclosure is further directed to plant parts from said plant. In some embodiments, the plant parts of any preced-ing embodiment include a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the plant parts of any preceding embodiment include a pod. In still other embodiments, the present disclosure is directed to a soybean plant having all the physiological and morpho-logical characteristics of the plant of any of the preceding embodiments. Accordingly, some embodiments include a plant part of the soybean plant of any of the preceding embodiments. In some embodiments, the plant part includes a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the part is a pod.

One aspect of the present disclosure is directed to an F1 hybrid soybean plant having '10020889166' as a parent wherein '10020889166' is grown from the seed of any of the preceding embodiments. Some embodiments include a pol-len grain or an ovule of the plant of any of the preceding embodiments. Some embodiments include a tissue culture of the plant of any of the preceding embodiments. Some embodiments include a soybean plant regenerated from said tissue culture, wherein the plant has all of the morphological and physiological characteristics of a soybean plant pro-duced by growing seed designated as '10020889166' having ATCC Accession Number PTA-127941. Some aspects of the present disclosure are directed to a method of making soybean seeds, said method including crossing the plant of any of the preceding embodiments with another soybean plant and harvesting seed therefrom. Some aspects of the present disclosure are directed to a method of producing a commodity plant product, including obtaining the plant of any of the preceding embodiments or a part thereof and producing said commodity plant product therefrom. In some embodiments, the commodity plant product is protein con-centrate, protein isolate, hulls, meal, flour, or oil. In still other aspects, the present disclosure is directed to a method of making a soybean variety '10020889166', said method including selecting seeds from the cross of one '10020889166' plant with another '10020889166' plant, a sample of '10020889166' soybean seed having been depos-ited under ATCC Accession Number PTA-127941.

In still another embodiment, the present invention is further directed to soybean plants, soybean parts from the soybean plants, and seeds produced therefrom where the soybean plant is isolated by the breeding method of the invention. In another embodiment, the present invention is directed to methods for producing a soybean plant contain-ing in its genetic material one or more transgenes and to the transgenic soybean plant produced by those methods. In another embodiment, the present invention is directed to methods for producing a male sterile soybean plant by introducing a nucleic acid molecule that confers male ste-rility into a soybean plant produced by growing '10020889166' soybean seed, and to male sterile soybean plants produced by such methods. In another embodiment, the present invention is directed to methods of producing an herbicide resistant soybean plant by introducing a gene conferring herbicide resistance into a soybean plant pro-duced by growing '10020889166' soybean seed, where the gene is selected from glyphosate, sulfonylurea, imidazoli-none, dicamba, glufosinate, phenoxy proprionic acid, L-phosphinothricin, cyclohexone, cyclohexanedione, triaz-ine, and benzonitrile. Certain embodiments are also directed to herbicide resistant soybean plants produced by such methods. In another embodiment, the present invention is directed to methods of producing a pest or insect resistant soybean plan by introducing a gene conferring pest or insect resistance into a soybean plant produced by growing '10020889166' soybean seed, and to pest or insect resistant soybean plants produced by such methods. In another embodiment, the present invention is directed to methods of producing a disease resistant soybean plant by introducing a gene conferring disease resistance into a soybean plant produced by growing '10020889166' soybean seed, and to disease resistant soybean plants produced by such methods. In another embodiment, the present invention is directed to methods of producing a soybean plant with a value-added trait by introducing a gene conferring a value-added trait into a soybean plant produced by growing '10020889166' soybean seed, where the gene encodes a protein selected from a ferritin, a nitrate reductase, and a monellin. Certain embodiments are also directed to soybean plants having a value-added trait produced by such methods.

In another embodiment, the present invention is directed to methods of introducing a desired trait into soybean variety '10020889166', by: (a) crossing a '10020889166' plant, where a sample of '10020889166' soybean seed was deposited under ATCC Accession Number PTA-127941, with a plant of another soybean variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a '10020889166' plant to produce backcross progeny plants; (d) selecting for backcross progeny plants that have the desired trait and all of the physiological and morphological characteristics of soybean variety '10020889166'; and (e) repeating steps (c) and (d) two or more times in succession to produce selected third or higher backcross progeny plants that comprise the desired trait. Certain embodiments are also directed to soybean plants produced by such methods, where the plants have the desired trait and all of the physiological and morphological characteristics of soybean variety '10020889166'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile. In other embodiments, the desired trait is insect or pest resistance and the insect or pest resistance is conferred by a transgene encoding a *Bacillus thuringiensis* endotoxin. In another embodiment, the present invention provides for single gene converted plants of '10020889166'.

The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring soybean gene or a transgene introduced through genetic engineering techniques.

One aspect of the present disclosure includes a soybean seed designated as '70020032728'. Some embodiments include a soybean plant produced by growing said seed. In other embodiments, the present disclosure is further directed to plant parts from said plant. In some embodiments, the plant parts of any preceding embodiment include a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the plant parts of any preceding embodiment include a pod. In still other embodiments, the present disclosure is directed to a soybean plant having all the physiological and morphological characteristics of the plant of any of the preceding embodiments. Accordingly, some embodiments include a plant part of the soybean plant of any of the preceding embodiments. In some embodiments, the plant part includes a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the part is a pod.

One aspect of the present disclosure is directed to an F1 hybrid soybean plant having '70020032728' as a parent wherein '70020032728' is grown from the seed of any of the preceding embodiments. Some embodiments include a pollen grain or an ovule of the plant of any of the preceding embodiments. Some embodiments include a tissue culture of the plant of any of the preceding embodiments. Some embodiments include a soybean plant regenerated from said tissue culture, wherein the plant has all of the morphological and physiological characteristics of a soybean plant produced by growing seed designated as '70020032728'. Some aspects of the present disclosure are directed to a method of making soybean seeds, said method including crossing the plant of any of the preceding embodiments with another soybean plant and harvesting seed therefrom. Some aspects of the present disclosure are directed to a method of producing a commodity plant product, including obtaining the plant of any of the preceding embodiments or a part thereof and producing said commodity plant product therefrom. In some embodiments, the commodity plant product is protein concentrate, protein isolate, hulls, meal, flour, or oil. In still other aspects, the present disclosure is directed to a method of making a soybean variety '70020032728', said method including selecting seeds from the cross of one '70020032728' plant with another '70020032728' plant.

In still another embodiment, the present invention is further directed to soybean plants, soybean parts from the soybean plants, and seeds produced therefrom where the soybean plant is isolated by the breeding method of the invention. In another embodiment, the present invention is directed to methods for producing a soybean plant containing in its genetic material one or more transgenes and to the transgenic soybean plant produced by those methods. In another embodiment, the present invention is directed to methods for producing a male sterile soybean plant by introducing a nucleic acid molecule that confers male sterility into a soybean plant produced by growing '70020032728' soybean seed, and to male sterile soybean plants produced by such methods. In another embodiment, the present invention is directed to methods of producing an herbicide resistant soybean plant by introducing a gene conferring herbicide resistance into a soybean plant produced by growing '70020032728' soybean seed, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant soybean plants produced by such methods. In another embodiment, the present invention is directed to methods of producing a pest or insect resistant soybean plan by introducing a gene conferring pest or insect resistance into a soybean plant produced by growing '70020032728' soybean seed, and to pest or insect resistant soybean plants produced by such methods. In another embodiment, the present invention is directed to methods of producing a disease resistant soybean plant by introducing a gene conferring disease resistance into a soybean plant produced by growing '70020032728' soybean seed, and to disease resistant soybean plants produced by such methods. In another embodiment, the present invention is directed to methods of producing a soybean plant with a value-added trait by introducing a gene conferring a value-added trait into a soybean plant produced by growing '70020032728' soybean seed, where the gene encodes a protein selected from a ferritin, a nitrate reductase, and a monellin. Certain embodiments are also directed to soybean plants having a value-added trait produced by such methods.

In another embodiment, the present invention is directed to methods of introducing a desired trait into soybean variety '70020032728', by: (a) crossing a '70020032728' plant with a plant of another soybean variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a '70020032728' plant to produce backcross progeny plants; (d) selecting for backcross progeny plants that have the desired trait and all of the physiological and morphological characteristics of soybean variety '70020032728'; and (e) repeating steps (c) and (d) two or more times in succession to produce selected third or higher backcross progeny plants that comprise the desired trait. Certain embodiments are also directed to soybean plants produced by such methods, where the plants have the desired trait and all of the physiological and morphological characteristics of soybean variety '70020032728'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile. In other embodiments, the desired trait is insect or pest resistance and the insect or pest resistance is conferred by a transgene encoding a *Bacillus thuringiensis* endotoxin. In another embodiment, the present invention provides for single gene converted plants of '70020032728'.

The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring soybean gene or a transgene introduced through genetic engineering techniques.

One aspect of the present disclosure includes a soybean seed designated as '70020032975'. Some embodiments include a soybean plant produced by growing said seed. In other embodiments, the present disclosure is further directed to plant parts from said plant. In some embodiments, the plant parts of any preceding embodiment include a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the plant parts of any preceding embodiment include a pod. In still other embodiments, the present disclosure is directed to a soybean plant having all the physiological and morphological characteristics of the plant of any of the preceding embodiments. Accordingly, some embodiments include a plant part of the soybean plant of any of the preceding embodiments. In some embodiments, the plant part includes a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the part is a pod.

One aspect of the present disclosure is directed to an F1 hybrid soybean plant having '70020032975' as a parent wherein '70020032975' is grown from the seed of any of the preceding embodiments. Some embodiments include a pollen grain or an ovule of the plant of any of the preceding embodiments. Some embodiments include a tissue culture of the plant of any of the preceding embodiments. Some embodiments include a soybean plant regenerated from said tissue culture, wherein the plant has all of the morphological and physiological characteristics of a soybean plant produced by growing seed designated as '70020032975'. Some aspects of the present disclosure are directed to a method of making soybean seeds, said method including crossing the plant of any of the preceding embodiments with another soybean plant and harvesting seed therefrom. Some aspects of the present disclosure are directed to a method of producing a commodity plant product, including obtaining the plant of any of the preceding embodiments or a part thereof and producing said commodity plant product therefrom. In some embodiments, the commodity plant product is protein concentrate, protein isolate, hulls, meal, flour, or oil. In still other aspects, the present disclosure is directed to a method of making a soybean variety '70020032975', said method including selecting seeds from the cross of one '70020032975' plant with another '70020032975' plant.

In still another embodiment, the present invention is further directed to soybean plants, soybean parts from the soybean plants, and seeds produced therefrom where the soybean plant is isolated by the breeding method of the invention. In another embodiment, the present invention is directed to methods for producing a soybean plant containing in its genetic material one or more transgenes and to the transgenic soybean plant produced by those methods. In another embodiment, the present invention is directed to methods for producing a male sterile soybean plant by introducing a nucleic acid molecule that confers male sterility into a soybean plant produced by growing '70020032975' soybean seed, and to male sterile soybean plants produced by such methods. In another embodiment, the present invention is directed to methods of producing an herbicide resistant soybean plant by introducing a gene conferring herbicide resistance into a soybean plant produced by growing '70020032975' soybean seed, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant soybean plants produced by such methods. In another embodiment, the present invention is directed to methods of producing a pest or insect resistant soybean plan by introducing a gene conferring pest or insect resistance into a soybean plant produced by growing '70020032975' soybean seed, and to pest or insect resistant soybean plants produced by such methods. In another embodiment, the present invention is directed to methods of producing a disease resistant soybean plant by introducing a gene conferring disease resistance into a soybean plant produced by growing '70020032975' soybean seed, and to disease resistant soybean plants produced by such methods. In another embodiment, the present invention is directed to methods of producing a soybean plant with a value-added trait by introducing a gene conferring a value-added trait into a soybean plant produced by growing '70020032975' soybean seed, where the gene encodes a protein selected from a ferritin, a nitrate reductase, and a monellin. Certain embodiments are also directed to soybean plants having a value-added trait produced by such methods.

In another embodiment, the present invention is directed to methods of introducing a desired trait into soybean variety '70020032975', by: (a) crossing a '70020032975' plant with a plant of another soybean variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) back-crossing the selected progeny plants with a '70020032975' plant to produce backcross progeny plants; (d) selecting for backcross progeny plants that have the desired trait and all of the physiological and morphological characteristics of soybean variety '70020032975'; and (e) repeating steps (c) and (d) two or more times in succession to produce selected third or higher backcross progeny plants that comprise the desired trait. Certain embodiments are also directed to soybean plants produced by such methods, where the plants have the desired trait and all of the physiological and morphological characteristics of soybean variety '70020032975'. In certain embodiments, the desired trait is herbicide resistance and the resistance is conferred to an herbicide selected from glyphosate, sulfonylurea, imidazoli-none, dicamba, glufosinate, phenoxy proprionic acid, L-phosphinothricin, cyclohexone, cyclohexanedione, triaz-ine, and benzonitrile. In other embodiments, the desired trait is insect or pest resistance and the insect or pest resistance is conferred by a transgene encoding a *Bacillus thuringiensis* endotoxin. In another embodiment, the present invention provides for single gene converted plants of '70020032975'.

The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring soybean gene or a transgene introduced through genetic engineering techniques.

One aspect of the present disclosure includes a soybean seed designated as '70020033154'. Some embodiments include a soybean plant produced by growing said seed. In other embodiments, the present disclosure is further directed to plant parts from said plant. In some embodiments, the plant parts of any preceding embodiment include a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the plant parts of any preceding embodiment include a pod. In still other embodiments, the present disclosure is directed to a soybean plant having all the physiological and morphological characteristics of the plant of any of the preceding embodiments. Accordingly, some embodiments include a plant part of the soybean plant of any of the preceding embodiments. In some embodiments, the plant part includes a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the part is a pod.

One aspect of the present disclosure is directed to an F1 hybrid soybean plant having '70020033154' as a parent wherein '70020033154' is grown from the seed of any of the preceding embodiments. Some embodiments include a pollen grain or an ovule of the plant of any of the preceding embodiments. Some embodiments include a tissue culture of the plant of any of the preceding embodiments. Some embodiments include a soybean plant regenerated from said tissue culture, wherein the plant has all of the morphological and physiological characteristics of a soybean plant produced by growing seed designated as '70020033154'. Some aspects of the present disclosure are directed to a method of making soybean seeds, said method including crossing the plant of any of the preceding embodiments with another soybean plant and harvesting seed therefrom. Some aspects of the present disclosure are directed to a method of pro-ducing a commodity plant product, including obtaining the plant of any of the preceding embodiments or a part thereof and producing said commodity plant product therefrom. In some embodiments, the commodity plant product is protein concentrate, protein isolate, hulls, meal, flour, or oil. In still other aspects, the present disclosure is directed to a method of making a soybean variety '70020033154', said method including selecting seeds from the cross of one '70020033154' plant with another '70020033154' plant.

In still another embodiment, the present invention is further directed to soybean plants, soybean parts from the soybean plants, and seeds produced therefrom where the soybean plant is isolated by the breeding method of the invention. In another embodiment, the present invention is directed to methods for producing a soybean plant contain-ing in its genetic material one or more transgenes and to the transgenic soybean plant produced by those methods. In another embodiment, the present invention is directed to methods for producing a male sterile soybean plant by introducing a nucleic acid molecule that confers male ste-rility into a soybean plant produced by growing '70020033154' soybean seed, and to male sterile soybean plants produced by such methods. In another embodiment, the present invention is directed to methods of producing an herbicide resistant soybean plant by introducing a gene conferring herbicide resistance into a soybean plant pro-duced by growing '70020033154' soybean seed, where the gene is selected from glyphosate, sulfonylurea, imidazoli-none, dicamba, glufosinate, phenoxy proprionic acid, L-phosphinothricin, cyclohexone, cyclohexanedione, triaz-ine, and benzonitrile. Certain embodiments are also directed to herbicide resistant soybean plants produced by such methods. In another embodiment, the present invention is directed to methods of producing a pest or insect resistant soybean plan by introducing a gene conferring pest or insect resistance into a soybean plant produced by growing '70020033154' soybean seed, and to pest or insect resistant soybean plants produced by such methods. In another embodiment, the present invention is directed to methods of producing a disease resistant soybean plant by introducing a gene conferring disease resistance into a soybean plant produced by growing '70020033154' soybean seed, and to disease resistant soybean plants produced by such methods. In another embodiment, the present invention is directed to methods of producing a soybean plant with a value-added trait by introducing a gene conferring a value-added trait into a soybean plant produced by growing '70020033154' soybean seed, where the gene encodes a protein selected from a ferritin, a nitrate reductase, and a monellin. Certain embodiments are also directed to soybean plants having a value-added trait produced by such methods.

In another embodiment, the present invention is directed to methods of introducing a desired trait into soybean variety '70020033154', by: (a) crossing a '70020033154' plant with a plant of another soybean variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) back-crossing the selected progeny plants with a '70020033154' plant to produce backcross progeny plants; (d) selecting for backcross progeny plants that have the desired trait and all of the physiological and morphological characteristics of soybean variety '70020033154'; and (e) repeating steps (c) and (d) two or more times in succession to produce selected third or higher backcross progeny plants that comprise the desired trait. Certain embodiments are also directed to soybean plants produced by such methods, where the plants have the desired trait and all of the physiological and morphological characteristics of soybean variety '70020033154'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile. In other embodiments, the desired trait is insect or pest resistance and the insect or pest resistance is conferred by a transgene encoding a *Bacillus thuringiensis* endotoxin. In another embodiment, the present invention provides for single gene converted plants of '70020033154'.

The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring soybean gene or a transgene introduced through genetic engineering techniques.

One aspect of the present disclosure includes a soybean seed designated as '20598563'. Some embodiments include a soybean plant produced by growing said seed. In other embodiments, the present disclosure is further directed to plant parts from said plant. In some embodiments, the plant parts of any preceding embodiment include a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the plant parts of any preceding embodiment include a pod. In still other embodiments, the present disclosure is directed to a soybean plant having all the physiological and morphological characteristics of the plant of any of the preceding embodiments. Accordingly, some embodiments include a plant part of the soybean plant of any of the preceding embodiments. In some embodiments, the plant part includes a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the part is a pod.

One aspect of the present disclosure is directed to an F1 hybrid soybean plant having '20598563' as a parent wherein '20598563' is grown from the seed of any of the preceding embodiments. Some embodiments include a pollen grain or an ovule of the plant of any of the preceding embodiments. Some embodiments include a tissue culture of the plant of any of the preceding embodiments. Some embodiments include a soybean plant regenerated from said tissue culture, wherein the plant has all of the morphological and physiological characteristics of a soybean plant produced by growing seed designated as '20598563'. Some aspects of the present disclosure are directed to a method of making soybean seeds, said method including crossing the plant of any of the preceding embodiments with another soybean plant and harvesting seed therefrom. Some aspects of the present disclosure are directed to a method of producing a commodity plant product, including obtaining the plant of any of the preceding embodiments or a part thereof and producing said commodity plant product therefrom. In some embodiments, the commodity plant product is protein concentrate, protein isolate, hulls, meal, flour, or oil. In still other aspects, the present disclosure is directed to a method of making a soybean variety '20598563', said method including selecting seeds from the cross of one '20598563' plant with another '20598563' plant.

In still another embodiment, the present invention is further directed to soybean plants, soybean parts from the soybean plants, and seeds produced therefrom where the soybean plant is isolated by the breeding method of the invention. In another embodiment, the present invention is directed to methods for producing a soybean plant containing in its genetic material one or more transgenes and to the transgenic soybean plant produced by those methods. In another embodiment, the present invention is directed to methods for producing a male sterile soybean plant by introducing a nucleic acid molecule that confers male sterility into a soybean plant produced by growing '20598563' soybean seed, and to male sterile soybean plants produced by such methods. In another embodiment, the present invention is directed to methods of producing an herbicide resistant soybean plant by introducing a gene conferring herbicide resistance into a soybean plant produced by growing '20598563' soybean seed, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant soybean plants produced by such methods. In another embodiment, the present invention is directed to methods of producing a pest or insect resistant soybean plan by introducing a gene conferring pest or insect resistance into a soybean plant produced by growing '20598563' soybean seed, and to pest or insect resistant soybean plants produced by such methods. In another embodiment, the present invention is directed to methods of producing a disease resistant soybean plant by introducing a gene conferring disease resistance into a soybean plant produced by growing '20598563' soybean seed, and to disease resistant soybean plants produced by such methods. In another embodiment, the present invention is directed to methods of producing a soybean plant with a value-added trait by introducing a gene conferring a value-added trait into a soybean plant produced by growing '20598563' soybean seed, where the gene encodes a protein selected from a ferritin, a nitrate reductase, and a monellin. Certain embodiments are also directed to soybean plants having a value-added trait produced by such methods.

In another embodiment, the present invention is directed to methods of introducing a desired trait into soybean variety '20598563', by: (a) crossing a '20598563' plant with a plant of another soybean variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a '20598563' plant to produce backcross progeny plants; (d) selecting for backcross progeny plants that have the desired trait and all of the physiological and morphological characteristics of soybean variety '20598563'; and (e) repeating steps (c) and (d) two or more times in succession to produce selected third or higher backcross progeny plants that comprise the desired trait. Certain embodiments are also directed to soybean plants produced by such methods, where the plants have the desired trait and all of the physiological and morphological characteristics of soybean variety '20598563'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile. In other embodiments, the desired trait is insect or pest resistance and the insect or pest resistance is conferred by a transgene encoding a *Bacillus thuringiensis* endotoxin. In another embodiment, the present invention provides for single gene converted plants of '20598563'.

The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring soybean gene or a transgene introduced through genetic engineering techniques.

One aspect of the present disclosure includes a soybean seed designated as '21097024'. Some embodiments include a soybean plant produced by growing said seed. In other embodiments, the present disclosure is further directed to plant parts from said plant. In some embodiments, the plant parts of any preceding embodiment include a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the plant parts of any preceding embodiment include a pod. In still other embodiments, the present disclosure is directed to a soybean plant having all the physiological and morphological characteristics of the plant of any of the preceding embodiments. Accordingly, some embodiments include a plant part of the soybean plant of any of the preceding embodiments. In some embodiments, the plant part includes a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the part is a pod.

One aspect of the present disclosure is directed to an F1 hybrid soybean plant having '21097024' as a parent wherein '21097024' is grown from the seed of any of the preceding embodiments. Some embodiments include a pollen grain or an ovule of the plant of any of the preceding embodiments. Some embodiments include a tissue culture of the plant of any of the preceding embodiments. Some embodiments include a soybean plant regenerated from said tissue culture, wherein the plant has all of the morphological and physiological characteristics of a soybean plant produced by growing seed designated as '21097024'. Some aspects of the present disclosure are directed to a method of making soybean seeds, said method including crossing the plant of any of the preceding embodiments with another soybean plant and harvesting seed therefrom. Some aspects of the present disclosure are directed to a method of producing a commodity plant product, including obtaining the plant of any of the preceding embodiments or a part thereof and producing said commodity plant product therefrom. In some embodiments, the commodity plant product is protein concentrate, protein isolate, hulls, meal, flour, or oil. In still other aspects, the present disclosure is directed to a method of making a soybean variety '21097024', said method including selecting seeds from the cross of one '21097024' plant with another '21097024' plant.

In still another embodiment, the present invention is further directed to soybean plants, soybean parts from the soybean plants, and seeds produced therefrom where the soybean plant is isolated by the breeding method of the invention. In another embodiment, the present invention is directed to methods for producing a soybean plant containing in its genetic material one or more transgenes and to the transgenic soybean plant produced by those methods. In another embodiment, the present invention is directed to methods for producing a male sterile soybean plant by introducing a nucleic acid molecule that confers male sterility into a soybean plant produced by growing '21097024' soybean seed, and to male sterile soybean plants produced by such methods. In another embodiment, the present invention is directed to methods of producing an herbicide resistant soybean plant by introducing a gene conferring herbicide resistance into a soybean plant produced by growing '21097024' soybean seed, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant soybean plants produced by such methods. In another embodiment, the present invention is directed to methods of producing a pest or insect resistant soybean plan by introducing a gene conferring pest or insect resistance into a soybean plant produced by growing '21097024' soybean seed, and to pest or insect resistant soybean plants produced by such methods. In another embodiment, the present invention is directed to methods of producing a disease resistant soybean plant by introducing a gene conferring disease resistance into a soybean plant produced by growing '21097024' soybean seed, and to disease resistant soybean plants produced by such methods. In another embodiment, the present invention is directed to methods of producing a soybean plant with a value-added trait by introducing a gene conferring a value-added trait into a soybean plant produced by growing '21097024' soybean seed, where the gene encodes a protein selected from a ferritin, a nitrate reductase, and a monellin. Certain embodiments are also directed to soybean plants having a value-added trait produced by such methods.

In another embodiment, the present invention is directed to methods of introducing a desired trait into soybean variety '21097024', by: (a) crossing a '21097024' plant with a plant of another soybean variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a '21097024' plant to produce backcross progeny plants; (d) selecting for backcross progeny plants that have the desired trait and all of the physiological and morphological characteristics of soybean variety '21097024'; and (e) repeating steps (c) and (d) two or more times in succession to produce selected third or higher backcross progeny plants that comprise the desired trait. Certain embodiments are also directed to soybean plants produced by such methods, where the plants have the desired trait and all of the physiological and morphological characteristics of soybean variety '21097024'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile. In other embodiments, the desired trait is insect or pest resistance and the insect or pest resistance is conferred by a transgene encoding a *Bacillus thuringiensis* endotoxin. In another embodiment, the present invention provides for single gene converted plants of '21097024'.

The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring soybean gene or a transgene introduced through genetic engineering techniques.

One aspect of the present disclosure includes a soybean seed designated as '10021387700'. Some embodiments include a soybean plant produced by growing said seed. In other embodiments, the present disclosure is further directed to plant parts from said plant. In some embodiments, the plant parts of any preceding embodiment include a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the plant parts of any preceding embodiment include a pod. In still other embodiments, the present disclosure is directed to a soybean plant having all the physiological and morphological characteristics of the plant of any of the preceding embodiments. Accordingly, some embodiments include a plant part of the soybean plant of any of the preceding embodiments. In some embodiments, the plant part includes a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the part is a pod.

One aspect of the present disclosure is directed to an F1 hybrid soybean plant having '10021387700' as a parent wherein '10021387700' is grown from the seed of any of the preceding embodiments. Some embodiments include a pollen grain or an ovule of the plant of any of the preceding embodiments. Some embodiments include a tissue culture of the plant of any of the preceding embodiments. Some embodiments include a soybean plant regenerated from said tissue culture, wherein the plant has all of the morphological and physiological characteristics of a soybean plant produced by growing seed designated as '10021387700'. Some aspects of the present disclosure are directed to a method of making soybean seeds, said method including crossing the plant of any of the preceding embodiments with another soybean plant and harvesting seed therefrom. Some aspects of the present disclosure are directed to a method of producing a commodity plant product, including obtaining the plant of any of the preceding embodiments or a part thereof and producing said commodity plant product therefrom. In some embodiments, the commodity plant product is protein concentrate, protein isolate, hulls, meal, flour, or oil. In still other aspects, the present disclosure is directed to a method of making a soybean variety '10021387700', said method including selecting seeds from the cross of one '10021387700' plant with another '10021387700' plant.

In still another embodiment, the present invention is further directed to soybean plants, soybean parts from the soybean plants, and seeds produced therefrom where the soybean plant is isolated by the breeding method of the invention. In another embodiment, the present invention is directed to methods for producing a soybean plant containing in its genetic material one or more transgenes and to the transgenic soybean plant produced by those methods. In another embodiment, the present invention is directed to methods for producing a male sterile soybean plant by introducing a nucleic acid molecule that confers male sterility into a soybean plant produced by growing '10021387700' soybean seed, and to male sterile soybean plants produced by such methods. In another embodiment, the present invention is directed to methods of producing an herbicide resistant soybean plant by introducing a gene conferring herbicide resistance into a soybean plant produced by growing '10021387700' soybean seed, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant soybean plants produced by such methods. In another embodiment, the present invention is directed to methods of producing a pest or insect resistant soybean plan by introducing a gene conferring pest or insect resistance into a soybean plant produced by growing '10021387700' soybean seed, and to pest or insect resistant soybean plants produced by such methods. In another embodiment, the present invention is directed to methods of producing a disease resistant soybean plant by introducing a gene conferring disease resistance into a soybean plant produced by growing '10021387700' soybean seed, and to disease resistant soybean plants produced by such methods. In another embodiment, the present invention is directed to methods of producing a soybean plant with a value-added trait by introducing a gene conferring a value-added trait into a soybean plant produced by growing '10021387700' soybean seed, where the gene encodes a protein selected from a ferritin, a nitrate reductase, and a monellin. Certain embodiments are also directed to soybean plants having a value-added trait produced by such methods.

In another embodiment, the present invention is directed to methods of introducing a desired trait into soybean variety '10021387700', by: (a) crossing a '10021387700' plant with a plant of another soybean variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a '10021387700' plant to produce backcross progeny plants; (d) selecting for backcross progeny plants that have the desired trait and all of the physiological and morphological characteristics of soybean variety '10021387700'; and (e) repeating steps (c) and (d) two or more times in succession to produce selected third or higher backcross progeny plants that comprise the desired trait. Certain embodiments are also directed to soybean plants produced by such methods, where the plants have the desired trait and all of the physiological and morphological characteristics of soybean variety '10021387700'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexanedione, triazine, and benzonitrile. In other embodiments, the desired trait is insect or pest resistance and the insect or pest resistance is conferred by a transgene encoding a *Bacillus thuringiensis* endotoxin. In another embodiment, the present invention provides for single gene converted plants of '10021387700'.

The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring soybean gene or a transgene introduced through genetic engineering techniques.

One aspect of the present disclosure includes a soybean seed designated as '10021389471'. Some embodiments include a soybean plant produced by growing said seed. In other embodiments, the present disclosure is further directed to plant parts from said plant. In some embodiments, the plant parts of any preceding embodiment include a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the plant parts of any preceding embodiment include a pod. In still other embodiments, the present disclosure is directed to a soybean plant having all the physiological and morphological characteristics of the plant of any of the preceding embodiments. Accordingly, some embodiments include a plant part of the soybean plant of any of the preceding embodiments. In some embodiments, the plant part includes a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the part is a pod.

One aspect of the present disclosure is directed to an F1 hybrid soybean plant having '10021389471' as a parent wherein '10021389471' is grown from the seed of any of the preceding embodiments. Some embodiments include a pollen grain or an ovule of the plant of any of the preceding embodiments. Some embodiments include a tissue culture of the plant of any of the preceding embodiments. Some embodiments include a soybean plant regenerated from said tissue culture, wherein the plant has all of the morphological and physiological characteristics of a soybean plant produced by growing seed designated as '10021389471'. Some aspects of the present disclosure are directed to a method of making soybean seeds, said method including crossing the plant of any of the preceding embodiments with another soybean plant and harvesting seed therefrom. Some aspects of the present disclosure are directed to a method of producing a commodity plant product, including obtaining the plant of any of the preceding embodiments or a part thereof and producing said commodity plant product therefrom. In some embodiments, the commodity plant product is protein concentrate, protein isolate, hulls, meal, flour, or oil. In still other aspects, the present disclosure is directed to a method of making a soybean variety '10021389471', said method including selecting seeds from the cross of one '10021389471' plant with another '10021389471' plant.

In still another embodiment, the present invention is further directed to soybean plants, soybean parts from the soybean plants, and seeds produced therefrom where the soybean plant is isolated by the breeding method of the invention. In another embodiment, the present invention is directed to methods for producing a soybean plant containing in its genetic material one or more transgenes and to the transgenic soybean plant produced by those methods. In another embodiment, the present invention is directed to methods for producing a male sterile soybean plant by introducing a nucleic acid molecule that confers male sterility into a soybean plant produced by growing '10021389471' soybean seed, and to male sterile soybean plants produced by such methods. In another embodiment, the present invention is directed to methods of producing an herbicide resistant soybean plant by introducing a gene conferring herbicide resistance into a soybean plant produced by growing '10021389471' soybean seed, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant soybean plants produced by such methods. In another embodiment, the present invention is directed to methods of producing a pest or insect resistant soybean plan by introducing a gene conferring pest or insect resistance into a soybean plant produced by growing '10021389471' soybean seed, and to pest or insect resistant soybean plants produced by such methods. In another embodiment, the present invention is directed to methods of producing a disease resistant soybean plant by introducing a gene conferring disease resistance into a soybean plant produced by growing '10021389471' soybean seed, and to disease resistant soybean plants produced by such methods. In another embodiment, the present invention is directed to methods of producing a soybean plant with a value-added trait by introducing a gene conferring a value-added trait into a soybean plant produced by growing '10021389471' soybean seed, where the gene encodes a protein selected from a ferritin, a nitrate reductase, and a monellin. Certain embodiments are also directed to soybean plants having a value-added trait produced by such methods.

In another embodiment, the present invention is directed to methods of introducing a desired trait into soybean variety '10021389471', by: (a) crossing a '10021389471' plant with a plant of another soybean variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a '10021389471' plant to produce backcross progeny plants; (d) selecting for backcross progeny plants that have the desired trait and all of the physiological and morphological characteristics of soybean variety '10021389471'; and (e) repeating steps (c) and (d) two or more times in succession to produce selected third or higher backcross progeny plants that comprise the desired trait. Certain embodiments are also directed to soybean plants produced by such methods, where the plants have the desired trait and all of the physiological and morphological characteristics of soybean variety '10021389471'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile. In other embodiments, the desired trait is insect or pest resistance and the insect or pest resistance is conferred by a transgene encoding a *Bacillus thuringiensis* endotoxin. In another embodiment, the present invention provides for single gene converted plants of '10021389471'.

The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring soybean gene or a transgene introduced through genetic engineering techniques.

One aspect of the present disclosure includes a soybean seed designated as '10021384531. Some embodiments include a soybean plant produced by growing said seed. In other embodiments, the present disclosure is further directed to plant parts from said plant. In some embodiments, the plant parts of any preceding embodiment include a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the plant parts of any preceding embodiment include a pod. In still other embodiments, the present disclosure is directed to a soybean plant having all the physiological and morphological characteristics of the plant of any of the preceding embodiments. Accordingly, some embodiments include a plant part of the soybean plant of any of the preceding embodiments. In some embodiments, the plant part includes a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the part is a pod.

One aspect of the present disclosure is directed to an F1 hybrid soybean plant having '10021384531' as a parent wherein '10021384531' is grown from the seed of any of the preceding embodiments. Some embodiments include a pollen grain or an ovule of the plant of any of the preceding embodiments. Some embodiments include a tissue culture of the plant of any of the preceding embodiments. Some embodiments include a soybean plant regenerated from said tissue culture, wherein the plant has all of the morphological and physiological characteristics of a soybean plant produced by growing seed designated as '10021384531'. Some aspects of the present disclosure are directed to a method of making soybean seeds, said method including crossing the plant of any of the preceding embodiments with another soybean plant and harvesting seed therefrom. Some aspects of the present disclosure are directed to a method of producing a commodity plant product, including obtaining the plant of any of the preceding embodiments or a part thereof and producing said commodity plant product therefrom. In some embodiments, the commodity plant product is protein concentrate, protein isolate, hulls, meal, flour, or oil. In still other aspects, the present disclosure is directed to a method of making a soybean variety '10021384531', said method including selecting seeds from the cross of one '10021384531' plant with another '10021384531' plant.

In still another embodiment, the present invention is further directed to soybean plants, soybean parts from the soybean plants, and seeds produced therefrom where the soybean plant is isolated by the breeding method of the invention. In another embodiment, the present invention is directed to methods for producing a soybean plant containing in its genetic material one or more transgenes and to the transgenic soybean plant produced by those methods. In another embodiment, the present invention is directed to methods for producing a male sterile soybean plant by introducing a nucleic acid molecule that confers male sterility into a soybean plant produced by growing '10021384531' soybean seed, and to male sterile soybean plants produced by such methods. In another embodiment, the present invention is directed to methods of producing an herbicide resistant soybean plant by introducing a gene conferring herbicide resistance into a soybean plant produced by growing '10021384531' soybean seed, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant soybean plants produced by such methods. In another embodiment, the present invention is directed to methods of producing a pest or insect resistant soybean plan by introducing a gene conferring pest or insect resistance into a soybean plant produced by growing '10021384531' soybean seed, and to pest or insect resistant soybean plants produced by such methods. In another embodiment, the present invention is directed to methods of producing a disease resistant soybean plant by introducing a gene conferring disease resistance into a soybean plant produced by growing '10021384531' soybean seed, and to disease resistant soybean plants produced by such methods. In another embodiment, the present invention is directed to methods of producing a soybean plant with a value-added trait by introducing a gene conferring a value-added trait into a soybean plant produced by growing '10021384531' soybean seed, where the gene encodes a protein selected from a ferritin, a nitrate reductase, and a monellin. Certain embodiments are also directed to soybean plants having a value-added trait produced by such methods.

In another embodiment, the present invention is directed to methods of introducing a desired trait into soybean variety '10021384531', by: (a) crossing a '10021384531' plant with a plant of another soybean variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a '10021384531' plant to produce backcross progeny plants; (d) selecting for backcross progeny plants that have the desired trait and all of the physiological and morphological characteristics of soybean variety '10021384531'; and (e) repeating steps (c) and (d) two or more times in succession to produce selected third or higher backcross progeny plants that comprise the desired trait. Certain embodiments are also directed to soybean plants produced by such methods, where the plants have the desired trait and all of the physiological and morphological characteristics of soybean variety '10021384531'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile. In other embodiments, the desired trait is insect or pest resistance and the insect or pest resistance is conferred by a transgene encoding a *Bacillus thuringiensis* endotoxin. In another embodiment, the present invention provides for single gene converted plants of '10021384531'.

The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring soybean gene or a transgene introduced through genetic engineering techniques.

One aspect of the present disclosure includes a soybean seed designated as '10021387127'. Some embodiments include a soybean plant produced by growing said seed. In other embodiments, the present disclosure is further directed to plant parts from said plant. In some embodiments, the plant parts of any preceding embodiment include a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the plant parts of any preceding embodiment include a pod. In still other embodiments, the present disclosure is directed to a soybean plant having all the physiological and morphological characteristics of the plant of any of the preceding embodiments. Accordingly, some embodiments include a plant part of the soybean plant of any of the preceding embodiments. In some embodiments, the plant part includes a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the part is a pod.

One aspect of the present disclosure is directed to an F1 hybrid soybean plant having '10021387127' as a parent wherein '10021387127' is grown from the seed of any of the preceding embodiments. Some embodiments include a pollen grain or an ovule of the plant of any of the preceding embodiments. Some embodiments include a tissue culture of the plant of any of the preceding embodiments. Some embodiments include a soybean plant regenerated from said tissue culture, wherein the plant has all of the morphological and physiological characteristics of a soybean plant produced by growing seed designated as '10021387127'. Some aspects of the present disclosure are directed to a method of making soybean seeds, said method including crossing the plant of any of the preceding embodiments with another soybean plant and harvesting seed therefrom. Some aspects of the present disclosure are directed to a method of producing a commodity plant product, including obtaining the plant of any of the preceding embodiments or a part thereof and producing said commodity plant product therefrom. In some embodiments, the commodity plant product is protein concentrate, protein isolate, hulls, meal, flour, or oil. In still other aspects, the present disclosure is directed to a method of making a soybean variety '10021387127', said method including selecting seeds from the cross of one '10021387127' plant with another '10021387127' plant.

In still another embodiment, the present invention is further directed to soybean plants, soybean parts from the soybean plants, and seeds produced therefrom where the soybean plant is isolated by the breeding method of the invention. In another embodiment, the present invention is directed to methods for producing a soybean plant containing in its genetic material one or more transgenes and to the transgenic soybean plant produced by those methods. In another embodiment, the present invention is directed to methods for producing a male sterile soybean plant by introducing a nucleic acid molecule that confers male sterility into a soybean plant produced by growing '10021387127' soybean seed, and to male sterile soybean plants produced by such methods. In another embodiment, the present invention is directed to methods of producing an herbicide resistant soybean plant by introducing a gene conferring herbicide resistance into a soybean plant produced by growing '10021387127' soybean seed, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant soybean plants produced by such methods. In another embodiment, the present invention is directed to methods of producing a pest or insect resistant soybean plan by introducing a gene conferring pest or insect resistance into a soybean plant produced by growing '10021387127' soybean seed, and to pest or insect resistant soybean plants produced by such methods. In another embodiment, the present invention is directed to methods of producing a disease resistant soybean plant by introducing a gene conferring disease resistance into a soybean plant produced by growing '10021387127' soybean seed, and to disease resistant soybean plants produced by such methods. In another embodiment, the present invention is directed to methods of producing a soybean plant with a value-added trait by introducing a gene conferring a value-added trait into a soybean plant produced by growing '10021387127' soybean seed, where the gene encodes a protein selected from a ferritin, a nitrate reductase, and a monellin. Certain embodiments are also directed to soybean plants having a value-added trait produced by such methods.

In another embodiment, the present invention is directed to methods of introducing a desired trait into soybean variety '10021387127', by: (a) crossing a '10021387127' plant with a plant of another soybean variety that contains a desired trait to produce progeny plants, where the desired trait is selected from male sterility; herbicide resistance; insect or pest resistance; modified bolting; and resistance to bacterial disease, fungal disease or viral disease: (b) selecting one or more progeny plants that have the desired trait; (c) backcrossing the selected progeny plants with a '10021387127' plant to produce backcross progeny plants; (d) selecting for backcross progeny plants that have the desired trait and all of the physiological and morphological characteristics of soybean variety '10021387127'; and (e) repeating steps (c) and (d) two or more times in succession to produce selected third or higher backcross progeny plants that comprise the desired trait. Certain embodiments are also directed to soybean plants produced by such methods, where the plants have the desired trait and all of the physiological and morphological characteristics of soybean variety '10021387127'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile. In other embodiments, the desired trait is insect or pest resistance and the insect or pest resistance is conferred by a transgene encoding a *Bacillus thuringiensis* endotoxin. In another embodiment, the present invention provides for single gene converted plants of '10021387127'.

The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring soybean gene or a transgene introduced through genetic engineering techniques.

One aspect of the present disclosure includes a soybean seed designated as '10020865219'. Some embodiments include a soybean plant produced by growing said seed. In other embodiments, the present disclosure is further directed to plant parts from said plant. In some embodiments, the plant parts of any preceding embodiment include a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the plant parts of any preceding embodiment include a pod. In still other embodiments, the present disclosure is directed to a soybean plant having all the physiological and morphological characteristics of the plant of any of the preceding embodiments. Accordingly, some embodiments include a plant part of the soybean plant of any of the preceding embodiments. In some embodiments, the plant part includes a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the part is a pod.

One aspect of the present disclosure is directed to an F1 hybrid soybean plant having '10020865219' as a parent wherein '10020865219' is grown from the seed of any of the preceding embodiments. Some embodiments include a pollen grain or an ovule of the plant of any of the preceding embodiments. Some embodiments include a tissue culture of the plant of any of the preceding embodiments. Some embodiments include a soybean plant regenerated from said tissue culture, wherein the plant has all of the morphological and physiological characteristics of a soybean plant produced by growing seed designated as '10020865219'. Some aspects of the present disclosure are directed to a method of making soybean seeds, said method including crossing the plant of any of the preceding embodiments with another soybean plant and harvesting seed therefrom. Some aspects of the present disclosure are directed to a method of producing a commodity plant product, including obtaining the plant of any of the preceding embodiments or a part thereof and producing said commodity plant product therefrom. In some embodiments, the commodity plant product is protein concentrate, protein isolate, hulls, meal, flour, or oil. In still other aspects, the present disclosure is directed to a method of making a soybean variety '10020865219', said method including selecting seeds from the cross of one '10020865219' plant with another '10020865219' plant.

In still another embodiment, the present invention is further directed to soybean plants, soybean parts from the soybean plants, and seeds produced therefrom where the soybean plant is isolated by the breeding method of the invention. In another embodiment, the present invention is directed to methods for producing a soybean plant containing in its genetic material one or more transgenes and to the transgenic soybean plant produced by those methods. In another embodiment, the present invention is directed to methods for producing a male sterile soybean plant by introducing a nucleic acid molecule that confers male sterility into a soybean plant produced by growing '10020865219' soybean seed, and to male sterile soybean plants produced by such methods. In another embodiment, the present invention is directed to methods of producing an herbicide resistant soybean plant by introducing a gene conferring herbicide resistance into a soybean plant produced by growing '10020865219' soybean seed, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant soybean plants produced by such methods. In another embodiment, the present invention is directed to methods of producing a pest or insect resistant soybean plan by introducing a gene conferring pest or insect resistance into a soybean plant produced by growing '10020865219' soybean seed, and to pest or insect resistant soybean plants produced by such methods. In another embodiment, the present invention is directed to methods of producing a disease resistant soybean plant by introducing a gene conferring disease resistance into a soybean plant produced by growing '10020865219' soybean seed, and to disease resistant soybean plants produced by such methods. In another embodiment, the present invention is directed to methods of producing a soybean plant with a value-added trait by introducing a gene conferring a value-added trait into a soybean plant produced by growing '10020865219' soybean seed, where the gene encodes a protein selected from a ferritin, a nitrate reductase, and a monellin. Certain embodiments are also directed to soybean plants having a value-added trait produced by such methods.

In another embodiment, the present invention is directed to methods of introducing a desired trait into soybean variety '10020865219', by: (a) crossing a '10020865219' plant with a plant of another soybean variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) back-crossing the selected progeny plants with a '10020865219' plant to produce backcross progeny plants; (d) selecting for backcross progeny plants that have the desired trait and all of the physiological and morphological characteristics of soybean variety '10020865219'; and (e) repeating steps (c) and (d) two or more times in succession to produce selected third or higher backcross progeny plants that comprise the desired trait. Certain embodiments are also directed to soybean plants produced by such methods, where the plants have the desired trait and all of the physiological and morphological characteristics of soybean variety '10020865219'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile. In other embodiments, the desired trait is insect or pest resistance and the insect or pest resistance is conferred by a transgene encoding a *Bacillus thuringiensis* endotoxin. In another embodiment, the present invention provides for single gene converted plants of '10020865219'.

The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring soybean gene or a transgene introduced through genetic engineering techniques.

One aspect of the present disclosure includes a soybean seed designated as '10021384221'. Some embodiments include a soybean plant produced by growing said seed. In other embodiments, the present disclosure is further directed to plant parts from said plant. In some embodiments, the plant parts of any preceding embodiment include a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the plant parts of any preceding embodiment include a pod. In still other embodiments, the present disclosure is directed to a soybean plant having all the physiological and morphological characteristics of the plant of any of the preceding embodiments. Accordingly, some embodiments include a plant part of the soybean plant of any of the preceding embodiments. In some embodiments, the plant part includes a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the part is a pod.

One aspect of the present disclosure is directed to an F1 hybrid soybean plant having '10021384221' as a parent wherein '10021384221' is grown from the seed of any of the preceding embodiments. Some embodiments include a pollen grain or an ovule of the plant of any of the preceding embodiments. Some embodiments include a tissue culture of the plant of any of the preceding embodiments. Some embodiments include a soybean plant regenerated from said tissue culture, wherein the plant has all of the morphological and physiological characteristics of a soybean plant produced by growing seed designated as '10021384221'. Some aspects of the present disclosure are directed to a method of making soybean seeds, said method including crossing the plant of any of the preceding embodiments with another soybean plant and harvesting seed therefrom. Some aspects of the present disclosure are directed to a method of producing a commodity plant product, including obtaining the plant of any of the preceding embodiments or a part thereof and producing said commodity plant product therefrom. In some embodiments, the commodity plant product is protein concentrate, protein isolate, hulls, meal, flour, or oil. In still other aspects, the present disclosure is directed to a method of making a soybean variety '10021384221', said method including selecting seeds from the cross of one '10021384221' plant with another '10021384221' plant.

In still another embodiment, the present invention is further directed to soybean plants, soybean parts from the soybean plants, and seeds produced therefrom where the soybean plant is isolated by the breeding method of the invention. In another embodiment, the present invention is directed to methods for producing a soybean plant containing in its genetic material one or more transgenes and to the transgenic soybean plant produced by those methods. In another embodiment, the present invention is directed to methods for producing a male sterile soybean plant by introducing a nucleic acid molecule that confers male sterility into a soybean plant produced by growing '10021384221' soybean seed, and to male sterile soybean plants produced by such methods. In another embodiment, the present invention is directed to methods of producing an herbicide resistant soybean plant by introducing a gene conferring herbicide resistance into a soybean plant produced by growing '10021384221' soybean seed, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant soybean plants produced by such methods. In another embodiment, the present invention is directed to methods of producing a pest or insect resistant soybean plan by introducing a gene conferring pest or insect resistance into a soybean plant produced by growing '10021384221' soybean seed, and to pest or insect resistant soybean plants produced by such methods. In another embodiment, the present invention is directed to methods of producing a disease resistant soybean plant by introducing a gene conferring disease resistance into a soybean plant produced by growing '10021384221' soybean seed, and to disease resistant soybean plants produced by such methods. In another embodiment, the present invention is directed to methods of producing a soybean plant with a value-added trait by introducing a gene conferring a value-added trait into a soybean plant produced by growing '10021384221' soybean seed, where the gene encodes a protein selected from a ferritin, a nitrate reductase, and a monellin. Certain embodiments are also directed to soybean plants having a value-added trait produced by such methods.

In another embodiment, the present invention is directed to methods of introducing a desired trait into soybean variety '10021384221', by: (a) crossing a '10021384221' plant with a plant of another soybean variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a '10021384221' plant to produce backcross progeny plants; (d) selecting for backcross progeny plants that have the desired trait and all of the physiological and morphological characteristics of soybean variety '10021384221'; and (e) repeating steps (c) and (d) two or more times in succession to produce selected third or higher backcross progeny plants that comprise the desired trait. Certain embodiments are also directed to soybean plants produced by such methods, where the plants have the desired trait and all of the physiological and morphological characteristics of soybean variety '10021384221'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile. In other embodiments, the desired trait is insect or pest resistance and the insect or pest resistance is conferred by a transgene encoding a *Bacillus thuringiensis* endotoxin. In another embodiment, the present invention provides for single gene converted plants of '10021384221'.

The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring soybean gene or a transgene introduced through genetic engineering techniques.

One aspect of the present disclosure includes a soybean seed designated as '21097118'. Some embodiments include a soybean plant produced by growing said seed. In other embodiments, the present disclosure is further directed to plant parts from said plant. In some embodiments, the plant parts of any preceding embodiment include a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the plant parts of any preceding embodiment include a pod. In still other embodiments, the present disclosure is directed to a soybean plant having all the physiological and morphological characteristics of the plant of any of the preceding embodiments. Accordingly, some embodiments include a plant part of the soybean plant of any of the preceding embodiments. In some embodiments, the plant part includes a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the part is a pod.

One aspect of the present disclosure is directed to an F1 hybrid soybean plant having '21097118' as a parent wherein '21097118' is grown from the seed of any of the preceding embodiments. Some embodiments include a pollen grain or an ovule of the plant of any of the preceding embodiments. Some embodiments include a tissue culture of the plant of any of the preceding embodiments. Some embodiments include a soybean plant regenerated from said tissue culture, wherein the plant has all of the morphological and physiological characteristics of a soybean plant produced by growing seed designated as '21097118'. Some aspects of the present disclosure are directed to a method of making soybean seeds, said method including crossing the plant of any of the preceding embodiments with another soybean plant and harvesting seed therefrom. Some aspects of the present disclosure are directed to a method of producing a commodity plant product, including obtaining the plant of any of the preceding embodiments or a part thereof and producing said commodity plant product therefrom. In some embodiments, the commodity plant product is protein concentrate, protein isolate, hulls, meal, flour, or oil. In still other aspects, the present disclosure is directed to a method of making a soybean variety '21097118', said method including selecting seeds from the cross of one '21097118' plant with another '21097118' plant.

In still another embodiment, the present invention is further directed to soybean plants, soybean parts from the soybean plants, and seeds produced therefrom where the soybean plant is isolated by the breeding method of the invention. In another embodiment, the present invention is directed to methods for producing a soybean plant containing in its genetic material one or more transgenes and to the transgenic soybean plant produced by those methods. In another embodiment, the present invention is directed to methods for producing a male sterile soybean plant by introducing a nucleic acid molecule that confers male sterility into a soybean plant produced by growing '21097118' soybean seed, and to male sterile soybean plants produced by such methods. In another embodiment, the present invention is directed to methods of producing an herbicide resistant soybean plant by introducing a gene conferring herbicide resistance into a soybean plant produced by growing '21097118' soybean seed, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant soybean plants produced by such methods. In another embodiment, the present invention is directed to methods of producing a pest or insect resistant soybean plan by introducing a gene conferring pest or insect resistance into a soybean plant produced by growing '21097118' soybean seed, and to pest or insect resistant soybean plants produced by such methods. In another embodiment, the present invention is directed to methods of producing a disease resistant soybean plant by introducing a gene conferring disease resistance into a soybean plant produced by growing '21097118' soybean seed, and to disease resistant soybean plants produced by such methods. In another embodiment, the present invention is directed to methods of producing a soybean plant with a value-added trait by introducing a gene conferring a value-added trait into a soybean plant produced by growing '21097118' soybean seed, where the gene encodes a protein selected from a ferritin, a nitrate reductase, and a monellin. Certain embodiments are also directed to soybean plants having a value-added trait produced by such methods.

In another embodiment, the present invention is directed to methods of introducing a desired trait into soybean variety '21097118', by: (a) crossing a '21097118' plant with a plant of another soybean variety that contains a desired trait to produce progeny plants, where the desired trait is selected from male sterility; herbicide resistance; insect or pest resistance: modified bolting; and resistance to bacterial disease, fungal disease or viral disease; (b) selecting one or more progeny plants that have the desired trait; (c) backcrossing the selected progeny plants with a '21097118' plant to produce backcross progeny plants; (d) selecting for backcross progeny plants that have the desired trait and all of the physiological and morphological characteristics of soybean variety '21097118'; and (e) repeating steps (c) and (d) two or more times in succession to produce selected third or higher backcross progeny plants that comprise the desired trait. Certain embodiments are also directed to soybean plants produced by such methods, where the plants have the desired trait and all of the physiological and morphological characteristics of soybean variety '21097118'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile. In other embodiments, the desired trait is insect or pest resistance and the insect or pest resistance is conferred by a transgene encoding a *Bacillus thuringiensis* endotoxin. In another embodiment, the present invention provides for single gene converted plants of '21097118'.

The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring soybean gene or a transgene introduced through genetic engineering techniques.

One aspect of the present disclosure includes a soybean seed designated as '10021389525'. and Some embodiments include a soybean plant produced by growing said seed. In other embodiments, the present disclosure is further directed to plant parts from said plant. In some embodiments, the plant parts of any preceding embodiment include a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the plant parts of any preceding embodiment include a pod. In still other embodiments, the present disclosure is directed to a soybean plant having all the physiological and morphological characteristics of the plant of any of the preceding embodiments. Accordingly, some embodiments include a plant part of the soybean plant of any of the preceding embodiments. In some embodiments, the plant part includes a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the part is a pod.

One aspect of the present disclosure is directed to an F1 hybrid soybean plant having '10021389525' as a parent wherein '10021389525' is grown from the seed of any of the preceding embodiments. Some embodiments include a pollen grain or an ovule of the plant of any of the preceding embodiments. Some embodiments include a tissue culture of the plant of any of the preceding embodiments. Some embodiments include a soybean plant regenerated from said tissue culture, wherein the plant has all of the morphological and physiological characteristics of a soybean plant produced by growing seed designated as '10021389525'. Some aspects of the present disclosure are directed to a method of making soybean seeds, said method including crossing the plant of any of the preceding embodiments with another soybean plant and harvesting seed therefrom. Some aspects of the present disclosure are directed to a method of producing a commodity plant product, including obtaining the plant of any of the preceding embodiments or a part thereof and producing said commodity plant product therefrom. In some embodiments, the commodity plant product is protein concentrate, protein isolate, hulls, meal, flour, or oil. In still other aspects, the present disclosure is directed to a method of making a soybean variety '10021389525', said method including selecting seeds from the cross of one '10021389525' plant with another '10021389525' plant.

In still another embodiment, the present invention is further directed to soybean plants, soybean parts from the soybean plants, and seeds produced therefrom where the soybean plant is isolated by the breeding method of the invention. In another embodiment, the present invention is directed to methods for producing a soybean plant containing in its genetic material one or more transgenes and to the transgenic soybean plant produced by those methods. In another embodiment, the present invention is directed to methods for producing a male sterile soybean plant by introducing a nucleic acid molecule that confers male sterility into a soybean plant produced by growing '10021389525' soybean seed, and to male sterile soybean plants produced by such methods. In another embodiment, the present invention is directed to methods of producing an herbicide resistant soybean plant by introducing a gene conferring herbicide resistance into a soybean plant produced by growing '10021389525' soybean seed, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant soybean plants produced by such methods. In another embodiment, the present invention is directed to methods of producing a pest or insect resistant soybean plan by introducing a gene conferring pest or insect resistance into a soybean plant produced by growing '10021389525' soybean seed, and to pest or insect resistant soybean plants produced by such methods. In another embodiment, the present invention is directed to methods of producing a disease resistant soybean plant by introducing a gene conferring disease resistance into a soybean plant produced by growing '10021389525' soybean seed, and to disease resistant soybean plants produced by such methods. In another embodiment, the present invention is directed to methods of producing a soybean plant with a value-added trait by introducing a gene conferring a value-added trait into a soybean plant produced by growing '10021389525' soybean seed, where the gene encodes a protein selected from a ferritin, a nitrate reductase, and a monellin. Certain embodiments are also directed to soybean plants having a value-added trait produced by such methods.

In another embodiment, the present invention is directed to methods of introducing a desired trait into soybean variety '10021389525', by: (a) crossing a '10021389525' plant with a plant of another soybean variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a '10021389525' plant to produce backcross progeny plants; (d) selecting for backcross progeny plants that have the desired trait and all of the physiological and morphological characteristics of soybean variety '10021389525'; and (e) repeating steps (c) and (d) two or more times in succession to produce selected third or higher backcross progeny plants that comprise the desired trait. Certain embodiments are also directed to soybean plants produced by such methods, where the plants have the desired trait and all of the physiological and morphological characteristics of soybean variety '10021389525'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile. In other embodiments, the desired trait is insect or pest resistance and the insect or pest resistance is conferred by a transgene encoding a *Bacillus thuringiensis* endotoxin. In another embodiment, the present invention provides for single gene converted plants of '10021389525'.

The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring soybean gene or a transgene introduced through genetic engineering techniques.

One aspect of the present disclosure includes a soybean seed designated as '10021384485'. Some embodiments include a soybean plant produced by growing said seed. In other embodiments, the present disclosure is further directed to plant parts from said plant. In some embodiments, the plant parts of any preceding embodiment include a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the plant parts of any preceding embodiment include a pod. In still other embodiments, the present disclosure is directed to a soybean plant having all the physiological and morphological characteristics of the plant of any of the preceding embodiments. Accordingly, some embodiments include a plant part of the soybean plant of any of the preceding embodiments. In some embodiments, the plant part includes a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof. In some embodiments, the part is a pod.

One aspect of the present disclosure is directed to an F1 hybrid soybean plant having '10021384485' as a parent wherein '10021384485' is grown from the seed of any of the preceding embodiments. Some embodiments include a pollen grain or an ovule of the plant of any of the preceding embodiments. Some embodiments include a tissue culture of the plant of any of the preceding embodiments. Some embodiments include a soybean plant regenerated from said tissue culture, wherein the plant has all of the morphological and physiological characteristics of a soybean plant produced by growing seed designated as '10021384485'. Some aspects of the present disclosure are directed to a method of making soybean seeds, said method including crossing the plant of any of the preceding embodiments with another soybean plant and harvesting seed therefrom. Some aspects of the present disclosure are directed to a method of producing a commodity plant product, including obtaining the plant of any of the preceding embodiments or a part thereof and producing said commodity plant product therefrom. In some embodiments, the commodity plant product is protein concentrate, protein isolate, hulls, meal, flour, or oil. In still other aspects, the present disclosure is directed to a method of making a soybean variety '10021384485', said method including selecting seeds from the cross of one '10021384485' plant with another '10021384485' plant.

In still another embodiment, the present invention is further directed to soybean plants, soybean parts from the soybean plants, and seeds produced therefrom where the soybean plant is isolated by the breeding method of the invention. In another embodiment, the present invention is directed to methods for producing a soybean plant containing in its genetic material one or more transgenes and to the transgenic soybean plant produced by those methods. In another embodiment, the present invention is directed to methods for producing a male sterile soybean plant by introducing a nucleic acid molecule that confers male sterility into a soybean plant produced by growing '10021384485' soybean seed, and to male sterile soybean plants produced by such methods. In another embodiment, the present invention is directed to methods of producing an herbicide resistant soybean plant by introducing a gene conferring herbicide resistance into a soybean plant produced by growing '10021384485' soybean seed, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant soybean plants produced by such methods. In another embodiment, the present invention is directed to methods of producing a pest or insect resistant soybean plan by introducing a gene conferring pest or insect resistance into a soybean plant produced by growing '10021384485' soybean seed, and to pest or insect resistant soybean plants produced by such methods. In another embodiment, the present invention is directed to methods of producing a disease resistant soybean plant by introducing a gene conferring disease resistance into a soybean plant produced by growing '10021384485' soybean seed, and to disease resistant soybean plants produced by such methods. In another embodiment, the present invention is directed to methods of producing a soybean plant with a value-added trait by introducing a gene conferring a value-added trait into a soybean plant produced by growing '10021384485' soybean seed, where the gene encodes a protein selected from a ferritin, a nitrate reductase, and a monellin. Certain embodiments are also directed to soybean plants having a value-added trait produced by such methods.

In another embodiment, the present invention is directed to methods of introducing a desired trait into soybean variety '10021384485', by: (a) crossing a '10021384485' plant with a plant of another soybean variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) back-crossing the selected progeny plants with a '10021384485' plant to produce backcross progeny plants; (d) selecting for backcross progeny plants that have the desired trait and all of the physiological and morphological characteristics of soybean variety '10021384485'; and (e) repeating steps (c) and (d) two or more times in succession to produce selected third or higher backcross progeny plants that comprise the desired trait. Certain embodiments are also directed to soybean plants produced by such methods, where the plants have the desired trait and all of the physiological and morphological characteristics of soybean variety '10021384485'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile. In other embodiments, the desired trait is insect or pest resistance and the insect or pest resistance is conferred by a transgene encoding a *Bacillus thuringiensis* endotoxin. In another embodiment, the present invention provides for single gene converted plants of '10021384485'.

The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring soybean gene or a transgene introduced through genetic engineering techniques.

DETAILED DESCRIPTION OF THE INVENTION

There are numerous steps in the development of novel, desirable soybean germplasm. Plant breeding begins with the analysis of problems and weaknesses of current soybean germplasms, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher seed yield, improved color, resistance to diseases and insects, tolerance to drought and heat, and better agronomic quality.

Choice of breeding or selection methods can depend on the mode of plant reproduction, the heritability of the trait(s) being improved, and the type of variety used commercially (e.g., F1 hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable variety. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program may include a periodic, objective evaluation of the efficiency of the breeding procedure. Evaluation criteria vary depending on the goal and objectives, and can include gain from selection per year based on comparisons to an appropriate standard, the overall value of the advanced breeding lines, and the number of successful varieties produced per unit of input (e.g., per year, per dollar expended, etc.).

Promising advanced breeding lines may be thoroughly tested and compared to appropriate standards in environments representative of the commercial target area(s) for at least three years. The best lines can then be candidates for new commercial varieties. Those still deficient in a few traits may be used as parents to produce new populations for further selection. These processes, which lead to the final step of marketing and distribution, may take from ten to twenty years from the time the first cross or selection is made.

One goal of soybean plant breeding is to develop new, unique, and genetically superior soybean varieties. A breeder can initially select and cross two or more parental lines, followed by repeated selfing and selection, producing many new genetic combinations. Moreover, a breeder can generate multiple different genetic combinations by crossing, selfing, and mutation breeding. A plant breeder can then select which germplasms to advance to the next generation. These germplasms may then be grown under different geographical, climatic, and soil conditions. Further selections can be made during, and at the end of, the growing season.

The development of commercial soybean varieties thus requires the development of parental soybean varieties, the crossing of these varieties, and the evaluation of the crosses. Pedigree breeding and recurrent selection breeding methods may be used to develop varieties from breeding populations. Breeding programs can be used to combine desirable traits from two or more varieties or various broad-based sources into breeding pools from which new varieties are developed by selfing and selection of desired phenotypes. The new varieties are crossed with other varieties and the hybrids from these crosses are evaluated to determine which have commercial potential.

Pedigree breeding is generally used for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population. Then, beginning in the $F_3$, the best individuals in the best families are selected. Replicated testing of families, or hybrid combinations involving individuals of these families, often follows in the Fa generation to improve the effectiveness of selection for traits with low heritability. At an advanced stage of inbreeding (i.e., $F_6$ and $F_7$), the best lines or mixtures of phenotypically similar lines are tested for potential release as new varieties.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding may be used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines with each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques known in the art that are available for the analysis, comparison and characterization of plant genotypes. Such techniques include, without limitation, DNA- or RNA-sequencing, CAPS Markers, ELISA, Western blot, microarrays, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), Differential Display Polymerase Chain Reaction (DD-PCR), Quantitative Real-Time Polymerase Chain Reaction (qRT-PCR), DNA Amplification Fingerprinting (DAF), Sequence Characterized Amplified Regions (SCARs), Amplified Fragment Length Polymorphisms (AFLPs), Simple Sequence Repeats (SSRs, which are also referred to as Microsatellites), and Single Nucleotide Polymorphisms (SNPs).

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding may also be used to introduce new traits into soybean varieties. Mutations that occur spontaneously or are artificially induced can be useful sources of variability for a plant breeder. The goal of artificial mutagenesis is to increase the rate of mutation for a desired characteristic. Mutation rates can be increased by many different means, including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.,* 77:889-892 (1989).

Additional non-limiting examples of breeding methods that may be used include, without limitation, those found in Allard, "Principles of plant breeding," John Wiley & Sons, NY, University of California, Davis, Calif., 50-98, 1960; Simmonds, "Principles of crop improvement," Longman, Inc., NY, 369-399, 1979; Sneep and Hendriksen, "Plant breeding perspectives," Wageningen (ed), Center for Agricultural Publishing and Documentation, 1979; Fehr, In: *Soybeans: Improvement, Production and Uses,"* 2d Ed., *Manograph* 16:249, 1987; Fehr, "Principles of cultivar development," Theory and Technique (Vol 1) and Crop Species Soybean (Vol 2), Iowa State Univ., Macmillan Pub. Co., NY, 360-376, 1987; Poehlman and Sleper, "Breeding Field Crops" Iowa State University Press, Ames, 1995; and Sprague and Dudley, eds., *Corn and Improvement,* 5th ed., 2006.

Definitions

In the claims, descriptions, and tables that follow, numerous terms are used and are defined as follows:

Allele: Any of one or more alternative forms of a gene locus, all of which relate to one trait or characteristic. In a diploid cell or organism, the two alleles of a given gene occupy corresponding loci on a pair of homologous chromosomes.

Cotyledon: A cotyledon is a type of seed leaf. The cotyledon contains the food storage tissues of the seed. Cotyledon color can be measured as a characteristic of a cultivar.

Flower color: Modern soybeans are characterized by two major flower colors, purple or white. Some cultivars are heterogeneous for flower color whereby some plants have purple flowers and some have white flowers.

Growth habit: Growth habit refers to stem termination in soybeans and the resultant differences in flower production. "Indeterminate" cultivars continue to grow during the reproductive phase, producing new branches and nodes after flowering is well underway. "Determinate" cultivars tend to delay the onset of flowering somewhat, and limit new node and branch development after flowering has been initiated. "Semi-determinate" cultivars continue to produce new vegetative growth during the reproductive phase but growth terminates more quickly than in indeterminate cultivars.

Hilum: Hilum refers to the point of attachment of soybean seed to maternal tissue.

Hilum color: In modern soybeans, hilum color may be black, brown, yellow, gray, buff, or imperfect black.

Lodging: Lodging is rated on a scale of 1 to 9. A score of 1 indicates erect plants. A score of 1.5 to 2.5 indicates erect to semi-erect plants. A score of 5 indicates plants are leaning at a 45 degree(s) angle in relation to the ground and a score of 9 indicates plants are lying on the ground.

Phytophthora Root Rot (PRR): Disorder in which the most recognizable symptom is stem rot. Brown discoloration ranges below the soil line and up to several inches above the soil line. Leaves often turn yellow, dull green and/or gray and may become brown and wilted, but remain attached to the plant.

Phytophthora Allele: Susceptibility or resistance to Phytophthora root rot races is affected by alleles such as Rps1a (denotes resistance to Races 1, 2, 10, 11, 13-18, 24, 26, 27, 31, 32, and 36); Rps1c (denotes resistance to Races 1-3, 6-11, 13, 15, 17, 21, 23, 24, 26, 28-30, 32, 34 and 36); Rps1k (denotes resistance to Races 1-11, 13-15, 17, 18, 21-24, 26, 36 and 37); Rps2 (denotes resistance to Races 1-5, 9-29, 33, 34 and 36-39); Rps3a (denotes resistance to Races 1-5, 8, 9, 11, 13, 14, 16, 18, 23, 25, 28, 29, 31-35); Rps6 (denotes resistance to Races 1-4, 10, 12, 14-16, 18-21 and 25); and Rps7 (denotes resistance to Races 2, 12, 16, 18, 19, 33, 35 and 36).

Predicted Relative Maturity (PRM) or Relative Maturity: The maturity grouping designated by the soybean industry over a given growing area. This figure is generally divided into tenths of a relative maturity group. Within narrow comparisons, the difference of a tenth of a relative maturity group equates very roughly to a day difference in maturity at harvest.

Protein (PRO), Protein Content, or Protein Percent: Seed protein content is measured and reported on a percentage basis.

Oil Content or Oil Percent: Seed oil content is measured and reported on a percentage basis.

Seed Protein Peroxidase Activity: Seed protein peroxidase activity is defined as a chemical taxonomic technique to separate varieties based on the presence or absence of the peroxidase enzyme in the seed coat. Soybean varieties may have high peroxidase activity (dark red color) or low peroxidase activity (no color).

Substantially Equivalent: A characteristic that, when compared, does not show a statistically significant difference (e.g., p=0.05) from the mean.

Overview of the Variety '10020720647'

Soybean variety '10020720647' is a transgenic soybean plant containing Enlist E3™ technology with an indeterminate plant habit. Soybean variety '10020720647' is the result of numerous generations of plant selections chosen for its resistance to Stem canker: southern (*Diaporthe phaseolorum* var. *meridionalis*), and Phytophthora root rot (*Phytophthora sojae* (Kaufmann & Gerdemann)) race 1; its tolerance to sulfonylurea; and its classification as maturity group V, subgroup 6.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '10020720647'.

Objective Description of the Variety '10020720647'

The cultivar description information (Table 1) provides a summary of soybean cultivar '10020720647' plant characteristics. Those of skill in the art will recognize that these are typical values that may vary due to environment and that other values that are substantially equivalent are within the scope of the invention. As used herein, "a soybean plant having the physiological and morphological characteristics of soybean cultivar '10020720647'" is a plant having the characteristics set forth in Table 1 when grown in the same environmental conditions.

TABLE 1

| Characteristic | Value |
|---|---|
| Morphology | |
| Seed Shape | Spherical |
| Seed Coat Color | Yellow |
| Seed Coat Luster | Opaque |
| Hilum Color | Buff |
| Peroxidase Activity | Negative |
| Protein content (%) | 36.60 |
| Oil content (%) | 18.50 |
| Cotyledon Color | Yellow |
| Hypocotyl Color | Green |
| Leaf Shape | Triangular base |
| Leaf Color | Medium Green |
| Flower Color | White |
| Pod Color | Tan |
| Pubescence Color | Light Tawny |
| Plant Habit | Indeterminate |
| Plant Type | Intermediate |
| Plant Height (inches) | 35.4 |
| Maturity Group | V |
| Maturity Subgroup | 6 |
| Fungal Disease Resistance | |
| Stem canker: southern (*Diaporthe phaseolorum* var. *meridionalis*) | Resistant |
| Phytophthora root rot (*Phytophthora sojae* (Kaufmann & Gerdemann)) race 1 | Resistant |
| Phytophthora root rot (*Phytophthora sojae* (Kaufmann & Gerdemann)) race 4 | Susceptible |
| Physiological Responses | |
| Sulfonylurea | Resistant |

Overview of the Variety '10020889109'

Soybean variety '10020889109' is a transgenic soybean plant containing Enlist E3™ technology with an indeterminate plant habit. Soybean variety '10020889109' is the result of numerous generations of plant selections chosen for its resistance to Stem canker: southern (*Diaporthe phaseolorum* var. *meridionalis*), and Phytophthora root rot (*Phytophthora sojae* (Kaufmann & Gerdemann)) races 1 and 4; its tolerance to sulfonylurea; and its classification as maturity group V, subgroup 0.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '10020889109'.

Objective Description of the Variety '10020889109'

The cultivar description information (Table 2) provides a summary of soybean cultivar '10020889109' plant characteristics. Those of skill in the art will recognize that these are typical values that may vary due to environment and that other values that are substantially equivalent are within the scope of the invention. As used herein, "a soybean plant having the physiological and morphological characteristics of soybean cultivar '10020889109'" is a plant having the characteristics set forth in Table 2 when grown in the same environmental conditions.

TABLE 2

| Characteristic | Value |
|---|---|
| Morphology | |
| Seed Shape | Spherical |
| Seed Coat Color | Yellow |
| Seed Coat Luster | Opaque |
| Hilum Color | Buff |
| Peroxidase Activity | Negative |
| Protein content (%) | 33.80 |
| Oil content (%) | 19.70 |
| Cotyledon Color | Yellow |
| Hypocotyl Color | Green |
| Leaf Shape | Triangular Base |
| Leaf Color | Medium Green |
| Flower Color | White |
| Pod Color | Tan |
| Pubescence Color | Gray |
| Plant Type | Intermediate |
| Plant Habit | Indeterminate |
| Plant Height | 43.3 |
| Maturity Group | V |
| Maturity Subgroup | 0 |
| Fungal Disease Resistance | |
| Stem canker: southern (*Diaporthe phaseolorum* var. *meridionalis*) | Resistant |
| Phytophthora root rot (*Phytophthora sojae* (Kaufmann & Gerdemann)) race 1 | Resistant |
| Phytophthora root rot (*Phytophthora sojae* (Kaufmann & Gerdemann)) race 4 | Resistant |
| Physiological Responses | |
| Sulfonylurea | Resistant |

Overview of the Variety '10020889166'

Soybean variety '10020889166' is a transgenic soybean plant containing Enlist E3™ technology with an indeterminate plant habit. Soybean variety '10020889166' is the result of numerous generations of plant selections chosen for its resistance to Stem canker: southern (*Diaporthe phaseolorum* var. *meridionalis*), and Phytophthora root rot (*Phytophthora sojae* (Kaufmann & Gerdemann)) race 1; its tolerance to sulfonylurea; and its classification as maturity group V, subgroup 1. Soybean variety '10020889166' is the result of crossing parent soybean varieties '1702205', also known within its internal breeding program as 'RC0410046138-5', and '10020508557', also known within its internal breeding program as 'CXCH161003509'. Parent variety '10020508557' was the source of the Enlist E3™ technology (corresponding to transgene event DAS-44406-6). Enlist E3™ confers tolerance of 2,4-Dichlorophenoxyacetic acid (2,4-D) herbicide, glufosinate herbicide, and glyphosate herbicide. To develop variety '10020889166', variety '1702205' and variety '10020508557' were initially crossed in October 2014 to April 2015 in Argentina. F1 seed resulting from the cross was planted from May 2015 to November 2015 in the United States, and F2 seeds were harvested in bulk. From November 2015 to April 2016, the F2 seeds were grown in Argentina for individual plant selection. From November 2016 to April 2017, progeny rows of the selected plants were grown in Argentina. Between October 2017 to April 2018, early generation candidate rows (ECRs) were evaluated for individual plant selections in Argentina. From May to October 2018, in the United States, the selected plants were trialed in ECRs by increments for desired traits. From October 2018 to April 2019, and then again from October 2019 to April 2020, further trials in ECRs by increments were conducted in Argentina.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '10020889166'.

Objective Description of the Variety '10020889166'

The cultivar description information (Table 3) provides a summary of soybean cultivar '10020889166' plant characteristics. Those of skill in the art will recognize that these are typical values that may vary due to environment and that other values that are substantially equivalent are within the scope of the invention. As used herein, "a soybean plant having the physiological and morphological characteristics of soybean cultivar '10020889166'" is a plant having the characteristics set forth in Table 3 when grown in the same environmental conditions.

TABLE 3

| Characteristic | Value |
|---|---|
| Morphology | |
| Seed Shape | Spherical |
| Seed Coat Color | Yellow |
| Seed Coat Luster | Opaque |
| Hilum Color | Buff |
| Peroxidase Activity | Negative |
| Protein content (%) | 33.60 |
| Oil content (%) | 20.90 |
| Cotyledon Color | Yellow |
| Hypocotyl Color | Green |
| Leaf Shape | Triangular Base |
| Leaf Color | Medium Green |
| Flower Color | White |
| Pod Color | Tan |
| Pubescence Color | Gray |
| Plant Type | Ramificated |
| Plant Height (inches) | 47.2 |
| Plant Habit | Indeterminate |
| Maturity Group | V |
| Maturity Subgroup | 1 |
| Fungal Disease Resistance | |
| Stem canker: southern (*Diaporthe phaseolorum* var. *meridionalis*) | Resistant |
| Phytophthora root rot (*Phytophthora sojae* (Kaufmann & Gerdemann)) race 1 | Resistant |
| Phytophthora root rot (*Phytophthora sojae* (Kaufmann & Gerdemann)) race 4 | Susceptible |
| Physiological Responses | |
| Sulfonylurea | Resistant |

Overview of the Variety '70020032728'

Soybean variety '70020032728' is a transgenic soybean plant containing Enlist E3™ technology with an indeterminate plant habit. Soybean variety '70020032728' is the result of numerous generations of plant selections chosen for its resistance to Stem canker: southern (*Diaporthe phaseolorum* var. *meridionalis*); its tolerance to sulfonylurea; and its classification as maturity group VI, subgroup 2.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '70020032728'.

Objective Description of the Variety '70020032728'

The cultivar description information (Table 4) provides a summary of soybean cultivar '70020032728' plant characteristics. Those of skill in the art will recognize that these are typical values that may vary due to environment and that other values that are substantially equivalent are within the scope of the invention. As used herein, "a soybean plant having the physiological and morphological characteristics of soybean cultivar '70020032728'" is a plant having the characteristics set forth in Table 4 when grown in the same environmental conditions.

TABLE 4

| Characteristic | Value |
|---|---|
| Morphology | |
| Seed Shape | Spherical |
| Seed Coat Color | Yellow |
| Seed Coat Luster | Opaque |
| Hilum Color | Buff |
| Peroxidase Activity | Positive |
| Protein Content (%) | 34.30 |
| Oil Content (%) | 19.20 |
| Cotyledon Color | Yellow |
| Hypocotyl Color | Green |
| Leaf Shape | Triangular Base |
| Leaf Color | Medium Green |
| Flower Color | White |
| Pod Color | Tan |
| Pubescence Color | Gray |
| Plant Type | Intermediate |
| Plant Height (inches) | 41.3 |
| Plant Habit | Indeterminate |
| Maturity Group | VI |
| Maturity Subgroup | 2 |
| Fungal Disease Resistance | |
| Stem canker: southern (*Diaporthe phaseolorum* var. *meridionalis*) | Resistant |
| Phytophthora root rot (*Phytophthora sojae* (Kaufmann & Gerdemann)) race 1 | Susceptible |
| Phytophthora root rot (*Phytophthora sojae* (Kaufmann & Gerdemann)) race 4 | Susceptible |
| Physiological Responses | |
| Sulfonylurea | Resistant |

Overview of the Variety '70020032975'

Soybean variety '70020032975' is a transgenic soybean plant containing Enlist E3™ technology with an indeterminate plant habit. Soybean variety '70020032975' is the result of numerous generations of plant selections chosen for its resistance to Stem canker: southern (*Diaporthe phaseolorum* var. *meridionalis*), and Phytophthora root rot (*Phytophthora sojae* (Kaufmann & Gerdemann)) race 1; its tolerance to sulfonylurea; and its classification as maturity group VI, subgroup 0.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '70020032975'.

Objective Description of the Variety '70020032975'

The cultivar description information (Table 5) provides a summary of soybean cultivar '70020032975' plant characteristics. Those of skill in the art will recognize that these are typical values that may vary due to environment and that other values that are substantially equivalent are within the scope of the invention. As used herein, "a soybean plant having the physiological and morphological characteristics of soybean cultivar '70020032975'" is a plant having the characteristics set forth in Table 5 when grown in the same environmental conditions.

TABLE 5

| Characteristic | Value |
|---|---|
| Morphology | |
| Seed Shape | Spherical |
| Seed Coat Color | Yellow |
| Seed Coat Luster | Opaque |
| Hilum Color | Buff |
| Peroxidase Activity (%) | Positive |
| Protein content (%) | 33.10 |
| Oil content (%) | 19.40 |
| Cotyledon Color | Yellow |
| Hypocotyl Color | Green |
| Leaf Shape | Triangular Base |
| Leaf Color | Medium Green |
| Flower Color | White |
| Pod Color | Tan |
| Pubescence Color | Gray |
| Plant Type | Intermediate |
| Plant Height (inches) | 45.3 |
| Plant Habit | Indeterminate |
| Maturity Group | VI |
| Maturity Subgroup | 0 |
| Fungal Disease Resistance | |
| Stem canker: southern (*Diaporthe phaseolorum* var. *meridionalis*) | Resistant |
| Phytophthora root rot (*Phytophthora sojae* (Kaufmann & Gerdemann)) race 1 | Resistant |
| Phytophthora root rot (*Phytophthora sojae* (Kaufmann & Gerdemann)) race 4 | Susceptible |
| Physiological Responses | |
| Sulfonylurea | Resistant |

Overview of the Variety '70020033154'

Soybean variety '70020033154' is a transgenic soybean plant containing Enlist E3™ technology with an indeterminate plant habit. Soybean variety '70020033154' is the result of numerous generations of plant selections chosen for its resistance to Stem canker: southern (*Diaporthe phaseolorum* var. *meridionalis*); its tolerance to sulfonylurea; and its classification as maturity group VI, subgroup 4.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '70020033154'.

Objective Description of the Variety '70020033154'

The cultivar description information (Table 6) provides a summary of soybean cultivar '70020033154' plant characteristics. Those of skill in the art will recognize that these are typical values that may vary due to environment and that other values that are substantially equivalent are within the scope of the invention. As used herein, "a soybean plant having the physiological and morphological characteristics of soybean cultivar '70020033154'" is a plant having the characteristics set forth in Table 6 when grown in the same environmental conditions.

TABLE 6

| Characteristic | Value |
|---|---|
| Morphology | |
| Seed Shape | Spherical |
| Seed Coat Color | Yellow |
| Seed Coat Luster | Opaque |
| Hilum Color | Buff |
| Peroxidase Activity | Positive |
| Peroxidase Content (%) | 36.20 |
| Oil Content (%) | 18.60 |
| Cotyledon Color | Yellow |
| Hypocotyl Color | Green |
| Leaf Shape | Triangular Base |
| Leaf Color | Medium Green |
| Flower Color | White |
| Pod Color | Tan |
| Pubescence Color | Gray |
| Plant Type | Intermediate |
| Plant Height (inches) | 41.3 |
| Plant Habit | Indeterminate |
| Maturity Group | VI |
| Maturity Subgroup | 4 |
| Fungal Disease Resistance | |
| Stem canker: southern (*Diaporthe phaseolorum* var. *meridionalis*) | Resistant |
| Phytophthora root rot (*Phytophthora sojae* (Kaufmann & Gerdemann)) race 1 | Susceptible |
| Phytophthora root rot (*Phytophthora sojae* (Kaufmann & Gerdemann)) race 4 | Susceptible |
| Physiological Responses | |
| Sulfonylurea | Resistant |

Overview of the Variety '20598563'

Soybean variety '20598563' is a transgenic soybean plant containing Enlist E3™ technology with an indeterminate plant habit. Soybean variety '20598563' is the result of numerous generations of plant selections chosen for its resistance to Stem canker: southern (*Diaporthe phaseolorum* var. *meridionalis*), and Phytophthora root rot (*Phytophthora sojae* (Kaufmann & Gerdemann)) races 1 and 4; its tolerance to sulfonylurea; and its classification as maturity group V, subgroup 0.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '20598563'.

Objective Description of the Variety '20598563'

The cultivar description information (Table 7) provides a summary of soybean cultivar '20598563' plant characteristics. Those of skill in the art will recognize that these are typical values that may vary due to environment and that other values that are substantially equivalent are within the scope of the invention. As used herein, "a soybean plant having the physiological and morphological characteristics of soybean cultivar '20598563'" is a plant having the characteristics set forth in Table 7 when grown in the same environmental conditions.

TABLE 7

| Characteristic | Value |
| --- | --- |
| Morphology | |
| Seed Shape | Spherical |
| Seed Coat Color | Yellow |
| Seed Coat Luster | Opaque |
| Hilum Color | Imperfect Black |
| Peroxidase Activity | Positive |
| Protein Content (%) | 34.10 |
| Oil Content (%) | 19.70 |
| Cotyledon Color | Yellow |
| Hypocotyl Color | Purple |
| Leaf Shape | Triangular Base |
| Leaf Color | Medium Green |
| Flower Color | Purple |
| Pod Color | Black |
| Pubescence Color | Gray |
| Plant Type | Intermediate |
| Plant Height (inches) | 41.3 |
| Plant Habit | Indeterminate |
| Maturity Group | V |
| Maturity Subgroup | 0 |
| Fungal Disease Resistance | |
| Stem canker: southern (*Diaporthe phaseolorum* var. *meridionalis*) | Resistant |
| Phytophthora root rot (*Phytophthora sojae* (Kaufmann & Gerdemann)) race 1 | Resistant |
| Phytophthora root rot (*Phytophthora sojae* (Kaufmann & Gerdemann)) race 4 | Resistant |
| Physiological Responses | |
| Sulfonylurea | Resistant |

Overview of the Variety '21097024'

Soybean variety '21097024' is a transgenic soybean plant containing Enlist E3™ technology with an indeterminate plant habit. Soybean variety '21097024' is the result of numerous generations of plant selections chosen for its resistance to Stem canker: southern (*Diaporthe phaseolorum* var. *meridionalis*), and its tolerance to sulfonylurea.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '21097024'.

Objective Description of the Variety '21097024'

The cultivar description information (Table 8) provides a summary of soybean cultivar '21097024' plant characteristics. Those of skill in the art will recognize that these are typical values that may vary due to environment and that other values that are substantially equivalent are within the scope of the invention. As used herein, "a soybean plant having the physiological and morphological characteristics of soybean cultivar '21097024'" is a plant having the characteristics set forth in Table 8 when grown in the same environmental conditions.

TABLE 8

| Characteristic | Value |
| --- | --- |
| Morphology | |
| Seed Shape | Spherical |
| Seed Coat Color | Yellow |
| Seed Coat Luster | Opaque |
| Hilum Color | Buff |
| Peroxidase Activity | positive |

TABLE 8-continued

| Characteristic | Value |
| --- | --- |
| Protein Content (%) | 32.50 |
| Oil content (%) | 20.10 |
| Cotyledon Color | Yellow |
| Hypocotyl Color | Green |
| Leaf Shape | Triangular Base |
| Leaf Color | Medium Green |
| Flower Color | White |
| Pod Color | Tan |
| Pubescence Color | Gray |
| Plant Type | Intermediate |
| Plant Height (inches) | 43.3 |
| Plant Habit | Indeterminate |
| Fungal Disease Resistance | |
| Stem canker: southern (*Diaporthe phaseolorum* var. *meridionalis*) | Resistant |
| Phytophthora root rot (*Phytophthora sojae* (Kaufmann & Gerdemann)) race 1 | Susceptible |
| Phytophthora root rot (*Phytophthora sojae* (Kaufmann & Gerdemann)) race 4 | Susceptible |
| Physiological Responses | |
| Sulfonylurea | Resistant |

Overview of the Variety '10021387700'

Soybean variety '10021387700' is a transgenic soybean plant containing Enlist E3™ technology with an indeterminate plant habit. Soybean variety '10021387700' is the result of numerous generations of plant selections chosen for its resistance to Stem canker: southern (*Diaporthe phaseolorum* var. *meridionalis*); its tolerance to sulfonylurea; and its classification as maturity group VI, subgroup 2.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '10021387700'.

Objective Description of the Variety '10021387700'

The cultivar description information (Table 9) provides a summary of soybean cultivar '10021387700' plant characteristics. Those of skill in the art will recognize that these are typical values that may vary due to environment and that other values that are substantially equivalent are within the scope of the invention. As used herein, "a soybean plant having the physiological and morphological characteristics of soybean cultivar '10021387700'" is a plant having the characteristics set forth in Table 9 when grown in the same environmental conditions.

TABLE 9

| Characteristic | Value |
| --- | --- |
| Morphology | |
| Seed Shape | Spherical |
| Seed Coat Color | Yellow |
| Seed Coat Luster | Opaque |
| Hilum Color | Buff |
| Peroxidase Activity | Positive |
| Protein Content (%) | 33.50 |
| Oil Content (%) | 21.20 |
| Cotyledon Color | Yellow |
| Hypocotyl Color | Green |
| Leaf Shape | Triangular Base |
| Leaf Color | Medium Green |
| Flower Color | White |
| Pod Color | Brown |

TABLE 9-continued

| Characteristic | Value |
|---|---|
| Pubescence Color | Gray |
| Plant Type | Intermediate |
| Plant Height (inches) | 47.2 |
| Plant Habit | Indeterminate |
| Maturity Group | VI |
| Maturity Subgroup | 2 |
| Fungal Disease Resistance | |
| Stem canker: southern (*Diaporthe phaseolorum* var. *meridionalis*) | Resistant |
| Phytophthora root rot (*Phytophthora sojae* (Kaufmann & Gerdemann)) race 1 | Susceptible |
| Phytophthora root rot (*Phytophthora sojae* (Kaufmann & Gerdemann)) race 4 | Susceptible |
| Physiological Responses | |
| Sulfonylurea | Resistant |

Overview of the Variety '10021389471'

Soybean variety '10021389471' is a transgenic soybean plant containing Enlist E3™ technology with an indeterminate plant habit. Soybean variety '10021389471' is the result of numerous generations of plant selections chosen for its resistance to Stem canker: southern (*Diaporthe phaseolorum* var. *meridionalis*) and Phytophthora root rot (*Phytophthora sojae* (Kaufmann & Gerdemann)) races 1 and 4.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '10021389471'.

Objective Description of the Variety '10021389471'

The cultivar description information (Table 10) provides a summary of soybean cultivar '10021389471' plant characteristics. Those of skill in the art will recognize that these are typical values that may vary due to environment and that other values that are substantially equivalent are within the scope of the invention. As used herein, "a soybean plant having the physiological and morphological characteristics of soybean cultivar '10021389471'" is a plant having the characteristics set forth in Table 10 when grown in the same environmental conditions.

TABLE 10

| Characteristic | Value |
|---|---|
| Morphology | |
| Seed Shape | Spherical |
| Seed Coat Color | Yellow |
| Seed Coat Luster | Opaque |
| Hilum Color | Buff |
| Peroxidase Activity | Positive |
| Protein Content (%) | 31.90 |
| Oil Content (%) | 21.10 |
| Cotyledon Color | Yellow |
| Hypocotyl Color | Green |
| Leaf Shape | Triangular Base |
| Leaf Color | Medium Green |
| Flower Color | White |
| Pod Color | Brown |
| Pubescence Color | Gray |
| Plant Type | Intermediate |
| Plant Height (inches) | 37.4 |
| Plant Habit | Indeterminate |

TABLE 10-continued

| Characteristic | Value |
|---|---|
| Fungal Disease Resistance | |
| Phytophthora root rot (*Phytophthora sojae* (Kaufmann & Gerdemann)) race 1 | Resistant |
| Phytophthora root rot (*Phytophthora sojae* (Kaufmann & Gerdemann)) race 4 | Resistant |
| Stem canker: southern (*Diaporthe phaseolorum* var. *meridionalis*) | Resistant |
| Physiological Responses | |
| Sulfonylurea | Susceptible |

Overview of the Variety '10021384531'

Soybean variety '10021384531' is a transgenic soybean plant containing Enlist E3™ technology with an indeterminate plant habit. Soybean variety '10021384531' is the result of numerous generations of plant selections chosen for its resistance to Stem canker: southern (*Diaporthe phaseolorum* var. *meridionalis*) and Phytophthora root rot (*Phytophthora sojae* (Kaufmann & Gerdemann)) race 1.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '10021384531'.

Objective Description of the Variety '10021384531'

The cultivar description information (Table 11) provides a summary of soybean cultivar '10021384531' plant characteristics. Those of skill in the art will recognize that these are typical values that may vary due to environment and that other values that are substantially equivalent are within the scope of the invention. As used herein, "a soybean plant having the physiological and morphological characteristics of soybean cultivar '10021384531'" is a plant having the characteristics set forth in Table 11 when grown in the same environmental conditions.

TABLE 11

| Characteristic | Value |
|---|---|
| Morphology | |
| Seed Shape | Spherical |
| Seed Coat Color | Yellow |
| Seed Coat Luster | Opaque |
| Hilum Color | Imperfect Black |
| Peroxidase Activity | Positive |
| Protein Content (%) | 36.60 |
| Oil Content (%) | 19.40 |
| Cotyledon Color | Yellow |
| Hypocotyl Color | Purple |
| Leaf Shape | Triangular Base |
| Leaf Color | Medium Green |
| Flower Color | Purple |
| Pod Color | Tan |
| Pubescence Color | Gray |
| Plant Type | Intermediate |
| Plant Height (inches) | 33.4 |
| Plant Habit | Indeterminate |
| Fungal Disease Resistance | |
| Stem canker: southern (*Diaporthe phaseolorum* var. *meridionalis*) | Resistant |
| Phytophthora root rot (*Phytophthora sojae* (Kaufmann & Gerdemann)) race 1 | Resistant |
| Phytophthora root rot (*Phytophthora sojae* (Kaufmann & Gerdemann)) race 4 | Susceptible |

TABLE 11-continued

| Characteristic | Value |
|---|---|
| Physiological Responses | |
| Sulfonylurea | Susceptible |

Overview of the Variety '10021387127'

Soybean variety '10021387127' is a transgenic soybean plant containing Enlist E3™ technology with an indeterminate plant habit. Soybean variety '10021387127' is the result of numerous generations of plant selections chosen for its resistance to Stem canker: southern (*Diaporthe phaseolorum* var. *meridionalis*).

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '10021387127'.

Objective Description of the Variety '10021387127'

The cultivar description information (Table 12) provides a summary of soybean cultivar '10021387127' plant characteristics. Those of skill in the art will recognize that these are typical values that may vary due to environment and that other values that are substantially equivalent are within the scope of the invention. As used herein, "a soybean plant having the physiological and morphological characteristics of soybean cultivar '10021387127'" is a plant having the characteristics set forth in Table 12 when grown in the same environmental conditions.

TABLE 12

| Characteristic | Value |
|---|---|
| Morphology | |
| Seed Shape | Spherical |
| Seed Coat Color | Yellow |
| Seed Coat Luster | Opaque |
| Hilum Color | Buff |
| Peroxidase Activity | Positive |
| Protein Content (%) | 35.10 |
| Oil Content (%) | 18.20 |
| Cotyledon Color | Yellow |
| Hypocotyl Color | Green |
| Leaf Shape | Triangular Base |
| Leaf Color | Medium Green |
| Flower Color | White |
| Pod Color | Brown |
| Pubescence Color | Gray |
| Plant Type | Intermediate |
| Plant Height (inches) | 47.2 |
| Plant Habit | Indeterminate |
| Fungal Disease Resistance | |
| Stem canker: southern (*Diaporthe phaseolorum* var. *meridionalis*) | Resistant |
| Phytophthora root rot (*Phytophthora sojae* (Kaufmann & Gerdemann)) race 1 | Susceptible |
| Phytophthora root rot (*Phytophthora sojae* (Kaufmann & Gerdemann)) race 4 | Susceptible |
| Physiological Responses | |
| Sulfonylurea | Susceptible |

Overview of the Variety '10020865219'

Soybean variety '10020865219' is a transgenic soybean plant containing Enlist E3™ technology with an indeterminate plant habit. Soybean variety '10020865219' is the result of numerous generations of plant selections chosen for its resistance to Stem canker: southern (*Diaporthe phaseolorum* var. *meridionalis*) and Phytophthora root rot (*Phytophthora sojae* (Kaufmann & Gerdemann)) races 1 and 4.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '10020865219'.

Objective Description of the Variety '10020865219'

The cultivar description information (Table 13) provides a summary of soybean cultivar '10020865219' plant characteristics. Those of skill in the art will recognize that these are typical values that may vary due to environment and that other values that are substantially equivalent are within the scope of the invention. As used herein, "a soybean plant having the physiological and morphological characteristics of soybean cultivar '10020865219'" is a plant having the characteristics set forth in Table 13 when grown in the same environmental conditions.

TABLE 13

| Characteristic | Value |
|---|---|
| Morphology | |
| Seed Shape | Spherical |
| Seed Coat Color | Yellow |
| Seed Coat Luster | Opaque |
| Hilum Color | Imperfect Black |
| Peroxidase Activity | Mix (84%+, 16%−) |
| Protein Content (%) | 34.52 |
| Oil Content (%) | 21.33 |
| Cotyledon Color | Yellow |
| Hypocotyl Color | Purple |
| Leaf Shape | Triangular Base |
| Leaf Color | Medium Green |
| Flower Color | Purple |
| Pod Color | Tan |
| Pubescence Color | Gray |
| Plant Type | Intermediate |
| Plant Habit | Indeterminate |
| Fungal Disease Resistance | |
| Phytophthora root rot (*Phytophthora sojae* (Kaufmann & Gerdemann)) race 1 | Resistant |
| Phytophthora root rot (*Phytophthora sojae* (Kaufmann & Gerdemann)) race 4 | Resistant |
| Stem canker: southern (*Diaporthe phaseolorum* var. *meridionalis*) | Resistant |
| Physiological Responses | |
| Sulfonylurea | Susceptible |

Overview of the Variety '10021384221'

Soybean variety '10021384221' is a transgenic soybean plant containing Enlist E3™ technology with an indeterminate plant habit. Soybean variety '10021384221' is the result of numerous generations of plant selections chosen for its resistance to Stem canker: southern (*Diaporthe phaseolorum* var. *meridionalis*), and Phytophthora root rot (*Phytophthora sojae* (Kaufmann & Gerdemann)) races 1 and 4; and its tolerance to sulfonylurea.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '10021384221'.

Objective Description of the Variety '10021384221'

The cultivar description information (Table 14) provides a summary of soybean cultivar '10021384221' plant characteristics. Those of skill in the art will recognize that these are typical values that may vary due to environment and that other values that are substantially equivalent are within the scope of the invention. As used herein, "a soybean plant having the physiological and morphological characteristics of soybean cultivar '10021384221'" is a plant having the characteristics set forth in Table 14 when grown in the same environmental conditions.

TABLE 14

| Characteristic | Value |
|---|---|
| Morphology | |
| Seed Shape | Spherical |
| Seed Coat Color | Yellow |
| Seed Coat Luster | Opaque |
| Hilum Color | Imperfect Black |
| Peroxidase Activity | Positive |
| Protein Content (%) | 33.70 |
| Oil Content (%) | 19.80 |
| Cotyledon Color | Yellow |
| Hypocotyl Color | Purple |
| Leaf Shape | Triangular Base |
| Leaf Color | Medium Green |
| Flower Color | Purple |
| Pod Color | Tan |
| Pubescence Color | Gray |
| Plant Type | Intermediate |
| Plant Height (inches) | 35.4 |
| Plant Habit | Indeterminate |
| Fungal Disease Resistance | |
| Stem canker: southern (*Diaporthe phaseolorum* var. *meridionalis*) | Resistant |
| Phytophthora root rot (*Phytophthora sojae* (Kaufmann & Gerdemann)) race 1 | Resistant |
| Phytophthora root rot (*Phytophthora sojae* (Kaufmann & Gerdemann)) race 4 | Resistant |
| Physiological Responses | |
| Sulfonylurea | Resistant |

Overview of the Variety '21097118'

Soybean variety '21097118' is a transgenic soybean plant containing Enlist E3™ technology with an indeterminate plant habit. Soybean variety '21097118' is the result of numerous generations of plant selections chosen for its resistance to Stem canker: southern (*Diaporthe phaseolorum* var. *meridionalis*), and its tolerance to sulfonylurea.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '21097118'.

Objective Description of the Variety '21097118'

The cultivar description information (Table 15) provides a summary of soybean cultivar '21097118' plant characteristics. Those of skill in the art will recognize that these are typical values that may vary due to environment and that other values that are substantially equivalent are within the scope of the invention. As used herein, "a soybean plant having the physiological and morphological characteristics of soybean cultivar '21097118'" is a plant having the characteristics set forth in Table 15 when grown in the same environmental conditions.

TABLE 15

| Characteristic | Value |
|---|---|
| Morphology | |
| Seed Shape | Spherical |
| Seed Coat Color | Yellow |
| Seed Coat Luster | Opaque |
| Hilum Color | Imperfect Black |
| Peroxidase Activity | Negative |
| Protein Content (%) | 33.50 |
| Oil Content (%) | 20.90 |
| Cotyledon Color | Yellow |
| Hypocotyl Color | Purple |
| Leaf Shape | Triangular Base |
| Leaf Color | Medium Green |
| Flower Color | Purple |
| Pod Color | Tan |
| Pubescence Color | Gray |
| Plant Type | Intermediate |
| Plant Height (inches) | 40.1 |
| Plant Habit | Indeterminate |
| Fungal Disease Resistance | |
| Stem canker: southern (*Diaporthe phaseolorum* var. *meridionalis*) | Resistant |
| Phytophthora root rot (*Phytophthora sojae* (Kaufmann & Gerdemann)) race 1 | Susceptible |
| Phytophthora root rot (*Phytophthora sojae* (Kaufmann & Gerdemann)) race 4 | Susceptible |
| Physiological Responses | |
| Sulfonylurea | Resistant |

Overview of the Variety '10021389525'

Soybean variety '10021389525' is a transgenic soybean plant containing Enlist E3™ technology with an indeterminate plant habit. Soybean variety '10021389525' is the result of numerous generations of plant selections chosen for its resistance to Stem canker: southern (*Diaporthe phaseolorum* var. *meridionalis*) and Phytophthora root rot (*Phytophthora sojae* (Kaufmann & Gerdemann)) races 1 and 4.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '10021389525'.

Objective Description of the Variety '10021389525'

The cultivar description information (Table 16) provides a summary of soybean cultivar '10021389525' plant characteristics. Those of skill in the art will recognize that these are typical values that may vary due to environment and that other values that are substantially equivalent are within the scope of the invention. As used herein, "a soybean plant having the physiological and morphological characteristics of soybean cultivar '10021389525'" is a plant having the characteristics set forth in Table 16 when grown in the same environmental conditions.

TABLE 16

| Characteristic | Value |
|---|---|
| Morphology | |
| Seed Shape | Spherical |
| Seed Coat Color | Yellow |
| Seed Coat Luster | Opaque |
| Hilum Color | Buff |
| Peroxidase Activity | Positive |
| Protein Content (%) | 34.70 |

TABLE 16-continued

| Characteristic | Value |
|---|---|
| Oil Content (%) | 18.20 |
| Cotyledon Color | Yellow |
| Hypocotyl Color | Green |
| Leaf Shape | Triangular Base |
| Leaf Color | Medium Green |
| Flower Color | White |
| Pod Color | Brown |
| Pubescence Color | Gray |
| Plant Type | Intermediate |
| Plant Height (inches) | 43.3 |
| Plant Habit | Indeterminate |
| Fungal Disease Resistance | |
| | |
| Phytophthora root rot (*Phytophthora sojae* (Kaufmann & Gerdemann)) race 1 | Resistant |
| Phytophthora root rot (*Phytophthora sojae* (Kaufmann & Gerdemann)) race 4 | Resistant |
| *Diaphorte Phaseolorum meridionalis* | Resistant |
| Physiological Responses | |
| | |
| Sulfonylurea | Susceptible |

Overview of the Variety '10021384485'

Soybean variety '10021384485' is a transgenic soybean plant containing Enlist E3™ technology with an indeterminate plant habit. Soybean variety '10021384485' is the result of numerous generations of plant selections chosen for its resistance to Stem canker: southern (*Diaporthe phaseolorum* var. *meridionalis*) and Phytophthora root rot (*Phytophthora sojae* (Kaufmann & Gerdemann)) races 1 and 4; and its tolerance to sulfonylurea.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '10021384485'.

Objective Description of the Variety '10021384485'

The cultivar description information (Table 17) provides a summary of soybean cultivar '10021384485' plant characteristics. Those of skill in the art will recognize that these are typical values that may vary due to environment and that other values that are substantially equivalent are within the scope of the invention. As used herein, "a soybean plant having the physiological and morphological characteristics of soybean cultivar '10021384485'" is a plant having the characteristics set forth in Table 17 when grown in the same environmental conditions.

TABLE 17

| Characteristic | Value |
|---|---|
| Morphology | |
| | |
| Seed Shape | Spherical |
| Seed Coat Color | Yellow |
| Seed Coat Luster | Opaque |
| Hilum Color | Imperfect Black |
| Peroxidase Activity | Positive |
| Protein Content (%) | 33.20 |
| Oil Content (%) | 20.10 |
| Cotyledon Color | Yellow |
| Hypocotyl Color | Purple |
| Leaf Shape | Triangular Base |
| Leaf Color | Medium Green |
| Flower Color | Purple |
| Pod Color | Tan |
| Pubescence Color | Gray |

TABLE 17-continued

| Characteristic | Value |
|---|---|
| Plant Type | Intermediate |
| Plant Height (inches) | 33.4 |
| Plant Habit | Indeterminate |
| Fungal Disease Resistance | |
| | |
| Stem canker: southern (*Diaporthe phaseolorum* var. *meridionalis*) | Resistant |
| Phytophthora root rot (*Phytophthora sojae* (Kaufmann & Gerdemann)) race 1 | Resistant |
| Phytophthora root rot (*Phytophthora sojae* (Kaufmann & Gerdemann)) race 4 | Resistant |
| Physiological Responses | |
| | |
| Sulfonylurea | Resistant |

Further Embodiments

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformed plants obtained with the protoplasm of the invention are intended to be within the scope of this invention.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Any DNA sequences, whether from a different species or from the same species, which are introduced into the genome using transformation or various breeding methods, are referred to herein collectively as "transgenes." Over the last fifteen to twenty years, several methods for producing transgenic plants have been developed. The present invention, in particular embodiments, also relates to transformed versions of the claimed lines.

Nucleic acids or polynucleotides refer to RNA or DNA that is linear or branched, single or double stranded, or a hybrid thereof. The term also encompasses RNA/DNA hybrids. These terms also encompass untranslated sequences located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. Polynucleotides may be produced by any means, including genomic preparations, cDNA preparations, in vitro synthesis, RT-PCR, and in vitro or in vivo transcription.

Plant transformation involves the construction of an expression vector that will function in plant cells. Such a vector contains DNA that contains a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed soybean plants using transformation methods as described below to incorporate transgenes into the genetic material of the soybean plant(s).

Expression Vectors for Soybean Transformation: Marker Genes

Expression vectors include at least one genetic marker, operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from the bacterial transposon Tn5, which when placed under the control of plant regulatory signals confers resistance to kanamycin. Fraley, et al., *PNAS,* 80:4803 (1983). Another commonly used selectable marker gene is the hygromycin phosphotransferase gene which confers resistance to the antibiotic hygromycin. Vanden Elzen, et al., *Plant Mol. Biol.,* 5:299 (1985).

Additional selectable marker genes of bacterial origin that confer resistance to antibiotics include gentamycin acetyl transferase, streptomycin phosphotransferase, aminoglycoside-3'-adenyl transferase, and the bleomycin resistance determinant. Hayford, et al., *Plant Physiol.,* 86:1216 (1988); Jones, et al., *Mol. Gen. Genet.,* 210:86 (1987); Svab, et al., *Plant Mol. Biol.,* 14:197 (1990); Hille, et al., *Plant Mol. Biol.,* 7:171 (1986). Other selectable marker genes confer resistance to herbicides such as glyphosate, glufosinate, or bromoxynil. Comai, et al., *Nature,* 317:741-744 (1985); Gordon-Kamm, et al., *Plant Cell,* 2:603-618 (1990); and Stalker, et al., *Science,* 242:419-423 (1988).

Selectable marker genes for plant transformation that are not of bacterial origin include, for example, mouse dihydrofolate reductase, plant 5-enolpyruvylshikimate-3-phosphate synthase, and plant acetolactate synthase. Eichholtz, et al., *Somatic Cell Mol. Genet.,* 13:67 (1987); Shah, et al., *Science,* 233:478 (1986); and Charest, et al., *Plant Cell Rep.,* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include α-glucuronidase (GUS), α-galactosidase (lacZ), luciferase, chloramphenicol, and acetyltransferase. Jefferson, R. A., *Plant Mol. Biol.,* 5:387 (1987); Teeri, et al., *EMBO J.,* 8:343 (1989); Koncz, et al., *PNAS,* 84:131 (1987); and DeBlock, et al., *EMBO J.,* 3:1681 (1984).

In vivo methods for visualizing GUS activity that do not require destruction of plant tissues are available. Molecular Probes, Publication 2908, IMAGENE GREEN, pp. 1-4 (1993) and Naleway, et al., *J. Cell Biol.,* 115: 151a (1991).

A gene encoding Green Fluorescent Protein (GFP) is now commonly utilized as a marker for gene expression in prokaryotic and eukaryotic cells. Chalfie, et al., *Science,* 263:802 (1994). GFP and GFP variants with altered excitation and emission spectra may be used as screenable markers.

Expression Vectors for Soybean Transformation: Promoters

Genes included in expression vectors must be driven by a nucleotide sequence containing a regulatory element (for example, a promoter). Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters:

An inducible promoter is operably linked to a gene for expression in soybean. Optionally, the inducible promoter is operably linked to a nucleotide sequence encoding a signal sequence which is operably linked to a gene for expression in soybean. With an inducible promoter, the rate of transcription increases in response to an inducing agent.

Any inducible promoter can be used in the present invention. See Ward, et al., *Plant Mol. Biol.,* 22:361-366 (1993). Exemplary inducible promoters include, but are not limited to, that from the ACEI system which responds to copper (Mett, et al., *PNAS,* 90:4567-4571 (1993)); the In2 promoter from maize which responds to benzenesulfonamide herbicide safeners (Hershey, et al., *Plant Mol. Bio.,* 4:679-90 (1991) and de Veylder, et al., *Plant Cell Physiol.* 38(5): 568-577 (1997)); or the bacterial Tet transcriptional repressor encoded by Tn10 (Gatz, et al., *Mol. Gen. Genet.,* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena, et al.,

*PNAS,* 88:10421 (1991) and Aoyama and Chua, *The Plant Journal* 11 (3): 605-612 (1997).

B. Constitutive Promoters:

A constitutive promoter is operably linked to a gene for expression in soybean or the constitutive promoter is oper- ably linked to a nucleotide sequence encoding a signal sequence which is operably linked to a gene for expression in soybean.

Many different constitutive promoters can be utilized in the present invention. Exemplary constitutive promoters include, but are not limited to, the promoters from plant viruses such as the 35S promoter from the Cauliflower Mosaic Virus (CaMV) (Odell, et al., *Nature,* 313:810-812 (1985)); plant promoters from genes such as actin (McElroy, et al., *Plant Cell,* 2:163-171 (1990)), ubiquitin (Christensen, et al., *Plant Mol. Biol.,* 12:619-632 (1989) and Christensen, et al., *Plant Mol. Biol.,* 18:675-689 (1992)), and histone H3 promoters such as a maize histone H3 promoter (Lepetit, et al., *Mol. Gen. Genet.,* 231:276-285 (1992) and Atanassova, et al., *Plant J.,* 2 (3): 291-300 (1992)); as well as synthetic promoters such as pEMU (Last, et al., *Theor. Appl. Genet.,* 81:581-588 (1991)), and promoters derived from *Agrobac- terium* genes such as mannopine synthase (mas) (Velten, et al., EMBO J., 3:2723-2730 (1984)). The ALS promoter, Xbal/Ncol fragment 5' to the *Brassica napus* ALS3 struc- tural gene (or a nucleotide sequence similar to said Xbal/ Ncol fragment), represents a particularly useful constitutive promoter due to its tissue general and high level expression. See, PCT Application No. WO 96/30530.

C. Tissue-Specific or Tissue-Preferred Promoters:

A tissue-specific promoter is operably linked to a gene for expression in soybean. Optionally, the tissue-specific pro- moter is operably linked to a nucleotide sequence encoding a signal sequence which is operably linked to a gene for expression in soybean. Plants transformed with a gene of interest operably linked to a tissue-specific promoter pro- duce the protein product of the transgene exclusively, or preferentially, in a specific tissue.

Any tissue-specific or tissue-preferred promoter can be utilized in the present invention. Exemplary tissue-specific or tissue-preferred promoters include, but are not limited to, a seed-specific promoter, such as that from the phaseolin gene (phas) (Murai, et al., *Science,* 23:476-482 (1983) and Sengupta-Gopalan, et al., *PNAS,* 82:3320-3324 (1985)); leaf-specific and light-induced promoters such as those derived from chlorophyll a/b binding (cab) protein genes or rubisco subunit genes (Simpson, et al., *EMBO J.,* 4 (11): 2723-2729 (1985) and Timko, et al., *Nature,* 318:579-582 (1985)); an anther-specific promoter such as that from the late pollen specific 52 (LAT52) gene (Twell, et al., *Mol. Gen. Genet.,* 217:240-245 (1989)); a pollen-specific promoter such as that from Zmg 13 (Guerrero, et al., *Mol. Gen. Genet.,* 224:161-168 (1990)); or a microspore-preferred promoter such as that from an anther-specific gene (apg) (Twell, et al., *Sex. Plant Reprod.,* 6:217-224 (1993)).

Signal Sequences for Targeting Proteins to Subcellular Compartments

Transport of proteins produced by transgenes to a sub- cellular compartment such as the chloroplast, vacuole, per- oxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein syn- thesis and processing, where the encoded protein is ulti- mately compartmentalized.

The presence of a signal sequence directs a polypeptide to either an intracellular organelle or subcellular compartment or for secretion to the apoplast. Many signal sequences are known in the art. See, for example, Becker, et al., *Plant Mol. Biol.,* 20:49 (1992); Close, P. S., Master's Thesis, Iowa State University (1993); Knox, C., et al., "Structure and Organi- zation of Two Divergent Alpha-Amylase Genes from Bar- ley," *Plant Mol. Biol.,* 9:3-17 (1987); Lerner, et al., *Plant Physiol.,* 91:124-129 (1989); Fontes, et al., *Plant Cell,* 3:483-496 (1991); Matsuoka, et al., *PNAS,* 88:834 (1991); Gould, et al., *J. Cell. Biol.,* 108:1657 (1989); Creissen, et al., *Plant J.,* 2:129 (1991); Kalderon, et al., A short amino acid sequence able to specify nuclear location, *Cell,* 39:499-509 (1984); and Steifel, et al., Expression of a maize cell wall hydroxyproline-rich glycoprotein gene in early leaf and root vascular differentiation, *Plant Cell,* 2:785-793 (1990).

Foreign Protein Genes and Agronomic Genes

A foreign protein can be produced in commercial quan- tities with transgenic plants according to the present inven- tion. Thus, techniques for the selection and propagation of transformed plants, which are well understood in the art, yield a plurality of transgenic plants which are harvested in a conventional manner. A foreign protein can then be extracted from a tissue of interest or from total biomass. Protein extraction from plant biomass can be accomplished by known methods which are discussed, for example, by Heney and Orr, *Anal. Biochem.,* 114:92-6 (1981). According to a preferred embodiment, a transgenic soybean plant is provided for commercial production of foreign proteins. In another preferred embodiment, the biomass of interest is seed.

For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see *Methods in Plant Molecu- lar Biology and Biotechnology,* Glick and Thompson Eds., 269:284, CRC Press, Boca Raton (1993). Map information concerning chromosomal location is useful for proprietary protection of a subject transgenic plant. If unauthorized propagation is undertaken and crosses made with other germplasm, the map of the integration region can be com- pared to similar maps for suspect plants, to determine if the latter have a common parentage with the subject plant. Map comparisons would involve hybridizations, RFLP, PCR, SSR, and sequencing, all of which are conventional tech- niques.

In some embodiments, a transgenic soybean variety pro- vided herein is a transgenic soybean plant containing Enlist E3™ technology (e.g., event DAS-44406-6), as described in the websites: bch[dot]cbd[dot]int/en/database/record?docu- mentID=105041, and www[dot]isaaa[dot]org/gmapproval- database/event/default.asp?EventID=345; and/or in one or more of the following U.S. Pat. Nos. 8,283,522; 8,916,751; 8,916,752; 9,540,655; 10,167,483; and 10,947,555. The Enlist E3™ technology confers glufosinate, glyphosate, and 2,4-D herbicide tolerance.

Likewise, by means of the present invention, agronomic genes can be expressed in transformed plants. More particu- larly, plants can be genetically engineered to express various phenotypes of agronomic interest. Exemplary genes impli- cated in this regard include, but are not limited to, those categorized below:

Genes that Confer Resistance to Pests or Disease

Plant defenses are often activated by specific interaction between the product of a disease resistance gene (R) in the plant and the product of a corresponding avirulence (Avr) gene in the pathogen. A plant line can be transformed with one or more cloned resistance genes to engineer plants that are resistant to specific pathogen strains. See, for example Jones et al. (*Science*, 266:7891, 1994) (cloning of the tomato Cf-9 gene for resistance to *Cladosporium fulvum*); Martin et al. (*Science*, 262:1432, 1993) (tomato Pto gene for resistance to *Pseudomonas syringae* pv. tomato); and Mindrinos et al. (*Cell*, 78(6): 1089-1099, 1994) (*Arabidopsis* RPS2 gene for resistance to *Pseudomonas syringae*).

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses. See Beachy et al. (*Ann. Rev. Phytopathol.*, 28:451, 1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody may also be used. See, for example, Tavladoraki et al. (*Nature*, 366:469, 1993), who show that transgenic plants expressing recombinant antibody genes are protected from virus attack. Virus resistance has also been described in, for example, U.S. Pat. Nos. 6,617,496; 6,608,241; 6,015,940; 6,013,864; 5,850,023 and 5,304,730.

Additional means of inducing whole-plant resistance to a pathogen include modulation of the systemic acquired resistance (SAR) or pathogenesis related (PR) genes, for example genes homologous to the *Arabidopsis thaliana* NIM1/NPR1/SAI1, and/or by increasing salicylic acid production (Ryals et al., *Plant Cell*, 8:1809-1819, 1996).

Logemann et al. (*Biotechnology*, 10:305, 1992), for example, disclose transgenic plants expressing a barley ribosome-inactivating gene that have an increased resistance to fungal disease. Plant defensins may be used to provide resistance to fungal pathogens (Thomma et al., *Planta*, 216:193-202, 2002). Other examples of fungal disease resistance are provided in U.S. Pat. Nos. 6,653,280; 6,573,361; 6,506,962; 6,316,407; 6,215,048; 5,516,671; 5,773,696; 6,121,436; and 6,316,407.

The use of the herbicide glyphosate for disease control in soybean plants containing event MON89788, which confers glyphosate tolerance, has also been described in U.S. Pat. No. 7,608,761.

Genes that Confer Resistance to Insects

One example of an insect resistance gene includes a *Bacillus thuringiensis* protein, a derivative thereof or a synthetic polypeptide modeled thereon. See, for example, Geiser et al. (*Gene*, 48 (1): 109-118, 1986), who disclose the cloning and nucleotide sequence of a *Bacillus thuringiensis* δ-endotoxin gene. Moreover, DNA molecules encoding δ-endotoxin genes can be purchased from the American Type Culture Collection, Manassas, Va., for example, under ATCC Accession Nos. 40098, 67136, 31995 and 31998. Another example is a lectin. See, for example, Van Damme et al. (*Plant Molec. Biol.*, 24:25, 1994), who disclose the nucleotide sequences of several *Clivia miniata* mannose-binding lectin genes. A vitamin-binding protein may also be used, such as avidin. See PCT Application No. US93/06487, the contents of which are hereby incorporated by reference. This application teaches the use of avidin and avidin homologues as larvicides against insect pests.

Another class of insect resistance genes are enzyme inhibitors, which include for example, protease or proteinase inhibitors, or amylase inhibitors. See, for example, Abe et al. (*J. Biol. Chem.*, 262:16793, 1987) (nucleotide sequence of rice cysteine proteinase inhibitor), Huub et al. (*Plant Molec. Biol.*, 21:985, 1993) (nucleotide sequence of cDNA encoding tobacco proteinase inhibitor I), and Sumitani et al. (*Biosci. Biotech. Biochem.*, 57:1243, 1993) (nucleotide sequence of *Streptomyces nitrosporeus* α-amylase inhibitor).

An insect-specific hormone or pheromone may also be used for insect resistance. See, for example, the disclosure by Hammock et al. (*Nature*, 344:458, 1990), of baculovirus expression of cloned juvenile hormone esterase, an inactivator of juvenile hormone; Gade and Goldsworthy (*Eds. Physiological System in Insects*, Elsevier Academic Press, Burlington, Mass., 2007), describing allostatins and their potential use in pest control; and Palli et al. (*Vitam. Horm.*, 73:59-100, 2005), disclosing use of ecdysteroid and ecdysteroid receptor in agriculture. The diuretic hormone receptor (DHR) was identified in Price et al. (*Insect Mol. Biol.*, 13:469-480, 2004) as a candidate target of insecticides.

Further examples include, without limitation, an insect-specific antibody or an immunotoxin derived therefrom and a developmental-arrestive protein. See Taylor et al. (Seventh Inn Symposium on Molecular Plant-Microbe Interactions, Edinburgh, Scotland, Abstract W97, 1994), who described enzymatic inactivation in transgenic tobacco via production of single-chain antibody fragments. Numerous other examples of insect resistance have been described. See, for example, U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245 and 5,763,241.

Genes that Confer Resistance to Herbicides

Numerous herbicide resistance genes are known and may be employed with the invention. An example is a gene conferring resistance to herbicides that inhibit the growing point or meristem, such as imidazalinones or sulfonylureas. Exemplary genes in this category code for mutant ALS and AHAS enzymes as described, for example, by Lee et al., *EMBO J.*, 7:1241, 1988; Gleen et al., *Plant Molec. Biology*, 18:1185-1187, 1992; and Miki et al., *Theor. Appl. Genet.*, 80:449, 1990.

Similarly, mutations of the aroA gene, which encodes 5-enolpyruvyl-3-phoshoshikimate synthetase, can result in an enzyme that is resistant to inhibition by glyphosate. A DNA molecule encoding a mutant aroA gene can be obtained under ATCC Accession Number 39256, and the nucleotide sequence of a mutant aroA gene is disclosed in U.S. Pat. No. 4,769,061 to Comai. A hygromycin B phosphotransferase gene from *E. coli* also confers resistance to glyphosate in tobacco callus and plants, as described by Penaloza-Vazquez et al., *Plant Cell Reports*, 14:482-487, 1995. Furthermore, European Patent Application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyltransferase gene is provided in European Patent Application No. 0 242 246 to Leemans et al. DeGree F. et al. (*Biotechnology*, 7:61, 1989), describe the production of transgenic plants that express chimeric bar genes coding for phosphinothricin acetyl transferase activity, which inactivates phosphinothricin. Exemplary genes conferring resistance to phenoxy propionic acids and cyclohexanediones, such as sethoxydim and haloxyfop, are the acetyl-coenzyme A carboxylase (Acc1) alleles described by Marshall et al., (*Theor. Appl. Genet.*, 83:435-442, 1992).

Genes are also known which confer resistance to herbicides that inhibit photosynthesis, such as a triazine (psbA and gs+ genes) and a benzonitrile (nitrilase gene). Przibilla et al. (*Plant Cell*, 3:169, 1991) describe the transformation of *Chlamydomonas* with plasmids encoding mutant variants of psbA. Nucleotide sequences for nitrilase genes, which can, for example, detoxify benzonitrile, are disclosed in U.S. Pat. No. 4,810,648 to Stalker. DNA molecules containing these genes are available under ATCC Accession Nos. 53435, 67441, and 67442. Cloning and expression of DNA coding for a glutathione S-transferase, which can also confer herbicide resistance, is described by Hayes et al. (Biochem. J., 285 (Pt 1): 173-180, 1992). Protoporphyrinogen oxidase (PPO), an enzyme involved in the biosynthesis of chlorophyll, is the target of the PPO-inhibitor class of herbicides. A PPO-inhibitor resistant PPO gene was identified in *Amaranthus tuberculatus* (Patzoldt et al., *PNAS*, 103 (33): 12329-2334, 2006). The herbicide methyl viologen inhibits $CO_2$ assimilation. Foyer et al. (*Plant Physiol.*, 109:1047-1057, 1995) describe a plant overexpressing glutathione reductase (GR) which is resistant to methyl viologen treatment.

Siminszky (Phytochemistry *Reviews*, 5:445-458, 2006) describes plant cytochrome P450-mediated detoxification of multiple, chemically unrelated classes of herbicides. Modified bacterial genes have been successfully demonstrated to confer resistance to atrazine, an herbicide that binds to the plastoquinone-binding membrane protein QB in photosystem II to inhibit electron transport. See, for example, studies by Cheung et al. (*PNAS*, 85 (2): 391-395, 1988), describing tobacco plants expressing the chloroplast psbA gene from an atrazine-resistant biotype of *Amaranthus hybridus* fused to the regulatory sequences of a nuclear gene, and Wang et al. (*Plant Biotech. J.*, 3:475-486, 2005), describing transgenic alfalfa, *Arabidopsis*, and tobacco plants expressing the atzA gene from *Pseudomonas* sp. that were able to detoxify atrazine.

Bayley et al. (*Theor. Appl. Genet.*, 83:645-649, 1992) describe using the 2,4-D monooxygenase gene tfdA from *Alcaligenes eutrophus* plasmid pJP5 for the creation of 2,4-D-resistant transgenic tobacco and cotton plants. U.S. Pat. App. Pub. No. 20030135879 describes the isolation of a gene for dicamba monooxygenase (DMO) from *Pseudomonas maltophilia* that is involved in the conversion of dicamba to a non-toxic 3,6-dichlorosalicylic acid and thus may be used for producing plants tolerant to this herbicide.

Other examples of herbicide resistance, include without limitation those described in U.S. Pat. Nos. 6,803,501; 6,448,476; 6,248,876; 6,225,114; 6,107,549; 5,866,775; 5,804,425; 5,633,435; 5,463,175.

Genes that Modify Fatty Acid, Phytate, and Carbohydrate Metabolism

Genes conferring modified fatty acid metabolism may also be employed with the present invention. For example, stearoyl-acyl carrier protein (stearoyl-ACP) desaturase genes may be used. See Knutzon et al. (*Proc. Natl. Acad. Sci. USA*, 89:2624, 1992). Various fatty acid desaturases have also been described. McDonough et al. describe a *Saccharomyces cerevisiae* OLE1 gene, which encodes Δ9-fatty acid desaturase, an enzyme which forms the monounsaturated palmitoleic (16:1) and oleic (18:1) fatty acids from palmitoyl (16:0) or stearoyl (18:0) CoA (*J. Biol. Chem.*, 267 (9): 5931-5936, 1992). Fox et al. describe a gene encoding a stearoyl-acyl carrier protein delta-9 desaturase from castor (*Proc. Natl. Acad. Sci. USA*, 90(6): 2486-2490, 1993). Reddy et al. describe Δ6- and Δ12-desaturases from the cyanobacteria *Synechocystis* responsible for the conversion of linoleic acid (18:2) to gamma-linolenic acid (18:3 gamma) (*Plant Mol. Biol.*, 22(2): 293-300, 1993). A gene from *Arabidopsis thaliana* that encodes an omega-3 desaturase has been identified (Arondel et al. *Science*, 258(5086): 1353-1355, 1992). Plant Δ9-desaturases (PCT Application Publ. No. WO 91/13972) and soybean and *Brassica* Δ15-desaturases (European Patent Application Publ. No. EP 0616644) have also been described. U.S. Pat. No. 7,622,632 describes fungal Δ15-desaturases and their use in plants. EP U.S. Pat. No. 1,656,449 describes Δ6-desaturases from *Primula* as well as soybean plants having an increased stearidonic acid (SDA, 18:4) content. U.S. Pat. App. Pub. No. 2008-0260929 describes expression of transgenic desaturase enzymes in corn plants, and improved fatty acid profiles resulting therefrom.

Modified oil production is disclosed, for example, in U.S. Pat. Nos. 6,444,876; 6,426,447; and 6,380,462. High oil production is disclosed, for example, in U.S. Pat. Nos. 6,495,739; 5,608,149; 6,483,008; and 6,476,295. Modified fatty acid content is disclosed, for example, in U.S. Pat. Nos. 6,828,475; 6,822,141; 6,770,465; 6,706,950; 6,660,849; 6,596,538; 6,589,767; 6,537,750; 6,489,461 and 6,459,018.

Phytate metabolism may also be modified by introduction of a phytase-encoding gene to enhance breakdown of phytate, adding more free phosphate to the transformed plant. For example, see Van Hartingsveldt et al. (*Gene*, 127:87, 1993), for disclosure of the nucleotide sequence of an *Aspergillus niger* phytase gene. In soybean, this, for example, could be accomplished by cloning and then reintroducing DNA associated with the single allele which is responsible for soybean mutants characterized by low levels of phytic acid and increased inorganic phosphate. See Raboy et al. (*Plant Physiol.*, 124 (1): 355-368, 2000), and Hitz et al. (*Plant Physiol.*, 128 (2): 650-660, 2002).

A number of genes are known that may be used to alter carbohydrate metabolism. For example, plants may be transformed with a gene coding for an enzyme that alters the branching pattern of starch. See Shiroza et al. (*J. Bacteriol.*, 170:810, 1988) (nucleotide sequence of *Streptococcus mutans* fructosyltransferase gene), Steinmetz et al. (*Mol. Gen. Genet.*, 20:220, 1985) (nucleotide sequence of *Bacillus subtilis* levansucrase gene), Pen et al. (*Biotechnology*, 10:292, 1992) (production of transgenic plants that express *Bacillus licheniformis* α-amylase), Elliot et al. (*Plant Molec. Biol.*, 21:515, 1993) (nucleotide sequences of tomato invertase genes), Søgaard et al. (*J. Biol. Chem.*, 268:22480, 1993b) (site-directed mutagenesis of barley α-amylase gene), and Fisher et al. (*Plant Physiol.*, 102:1045, 1993) (maize endosperm starch branching enzyme II). The Z10 gene encoding a 10 kD zein storage protein from maize may also be used to alter the quantities of 10 kD zein protein in plant cells relative to other components (Kirihara et al., *Gene*, 71 (2): 359-370, 1988).

Genes Encoding Additional Traits

Additional traits can be introduced into a soybean variety of the present invention. A non-limiting example of such a trait is a coding sequence which decreases RNA and/or protein levels for one or more genes of interest. The decreased RNA and/or protein levels may be achieved through RNAi methods, such as those described in U.S. Pat. No. 6,506,559 to Fire and Mellow.

Another trait that may find use with the soybean varieties of the present invention is a sequence which allows for site-specific recombination. Examples of such sequences include the flipase recognition (FRT) target sequences which are recognized by the flippase (FLP) recombinase (Zhu and Sadowski, *J. Biol. Chem.*, 270:23044-23054, 1995); and the LOX target sequence, for directing DNA recombination with the CRE recombinase (Sauer, *Mol. Cell. Biol.*, 7:2087-2096, 1987). The recombinase genes can be encoded at any location within the genome of the soybean plant, and are active in the hemizygous state.

It may also be desirable to make soybean plants more tolerant to or more easily transformed with *Agrobacterium tumefaciens*. For example, expression of p53 and iap, two baculovirus cell-death suppressor genes, inhibited cell death of maize tissues triggered by *Agrobacterium* infection. Additional targets can include plant-encoded proteins that interact with the *Agrobacterium* virulence (Vir) genes; enzymes involved in plant cell wall formation; and histones, histone acetyltransferases and histone deacetylases (reviewed in Gelvin, *Microbiology* & *Mol. Biol. Reviews*, 67:16-37, 2003).

In addition to the modification of oil, fatty acid or phytate content described above, it may additionally be beneficial to modify the amounts or levels of other compounds. For example, the amount or composition of antioxidants can be altered. See, for example, U.S. Pat. No. 6,787,618; U.S. Pat. App. Pub. No. 20040034886 and International Patent App. Pub. No. WO 00/68393, which disclose the manipulation of antioxidant levels, and International Patent App. Pub. No. WO 03/082899, which discloses the manipulation of an antioxidant biosynthetic pathway.

Additionally, seed amino acid content may be manipulated. U.S. Pat. No. 5,850,016 and International Patent App. Pub. No. WO 99/40209 disclose the alteration of the amino acid compositions of seeds. U.S. Pat. Nos. 6,080,913 and 6,127,600 disclose methods of increasing accumulation of essential amino acids in seeds.

U.S. Pat. No. 5,559,223 describes synthetic storage proteins in which the levels of essential amino acids can be manipulated. International Patent App. Pub. No. WO 99/29882 discloses methods for altering amino acid content of proteins. International Patent App. Pub. No. WO 98/20133 describes proteins with enhanced levels of essential amino acids. International Patent App. Pub. No. WO 98/56935 and U.S. Pat. Nos. 6,346,403, 6,441,274 and 6,664,445 disclose plant amino acid biosynthetic enzymes. International Patent App. Pub. No. WO 98/45458 describes synthetic seed proteins having a higher percentage of essential amino acids than wild-type.

U.S. Pat. No. 5,633,436 discloses plants comprising a higher content of sulfur-containing amino acids; U.S. Pat. No. 5,885,801 discloses plants comprising a high threonine content; U.S. Pat. Nos. 5,885,802 and 5,912,414 disclose plants comprising a high methionine content; U.S. Pat. No. 5,990,389 discloses plants comprising a high lysine content; U.S. Pat. No. 6,459,019 discloses plants comprising an increased lysine and threonine content; International Patent App. Pub. No. WO 98/42831 discloses plants comprising a high lysine content; International Patent App. Pub. No. WO 96/01905 discloses plants comprising a high threonine content and International Patent App. Pub. No. WO 95/15392 discloses plants comprising a high lysine content.

Genes that Control Male-Sterility

Genetic male sterility is available in soybeans and, although not required for crossing soybean plants, can increase the efficiency with which hybrids are made, in that it can eliminate the need to physically emasculate the soybean plant used as a female in a given cross. (Brim and Stuber, Crop Sci., 13:528-530, 1973). Herbicide-inducible male sterility systems have also been described. (U.S. Pat. No. 6,762,344).

Where one desires to employ male-sterility systems, it may be beneficial to also utilize one or more male-fertility restorer genes. For example, where cytoplasmic male sterility (CMS) is used, hybrid seed production requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful where the vegetative tissue of the soybean plant is utilized, but in many cases the seeds will be deemed the most valuable portion of the crop, so fertility of the hybrids in these crops must be restored. Therefore, one aspect of the present invention is directed to plants of the soybean variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485', comprising a genetic locus capable of restoring male fertility in an otherwise male-sterile plant. Examples of male-sterility genes and corresponding restorers which could be employed with the plants of the invention are well known to those of skill in the art of plant breeding (see, e.g., U.S. Pat. Nos. 5,530,191 and 5,684,242).

Methods for Soybean Transformation

Numerous methods for plant transformation have been developed, including biological and physical plant transformation protocols. See, for example, Miki, et al., "Procedures for Introducing Foreign DNA into Plants" in *Methods in Plant Molecular Biology and Biotechnology*, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in *Methods in Plant Molecular Biology and Biotechnology*, Glick and Thompson Eds., CRC Press, Inc., Boca Raton, pp. 89-119 (1993).

A. *Agrobacterium*-Mediated Transformation:

One method for introducing an expression vector into plants is based on the natural transformation system of *Agrobacterium*. See, for example, Horsch, et al., *Science*, 227:1229 (1985); Curtis, et al., *Journal of Experimental Botany*, 45:279, 1441-1449 (1994); Torres, et al., *Plant Cell Tissue and Organ Culture*, 34:3, 279-285 (1993); and Dinant, et al., *Molecular Breeding*, 3:1, 75-86 (1997). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*, 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Rep.*, 8:238 (1989). See also, U.S. Pat. No. 5,591,616 issued Jan. 7, 1997.

B. Direct Gene Transfer:

Several methods of plant transformation collectively referred to as direct gene transfer have been developed as an alternative to *Agrobacterium*-mediated transformation. A generally applicable method of plant transformation is microprojectile-mediated transformation where DNA is carried on the surface of microprojectiles measuring 1 μm to 4 μm. The expression vector is introduced into plant tissues with a biolistic device that accelerates the microprojectiles to speeds of 300 m/s to 600 m/s, which is sufficient to penetrate plant cell walls and membranes. Russell, D. R., et al., *Plant Cell Rep.*, 12 (3, January), 165-169 (1993); Aragao, F. J. L., et al., *Plant Mol. Biol.*, 20 (2, October), 357-359 (1992); Aragao, F. J. L., et al., *Plant Cell Rep.*, 12 (9, July), 483-490 (1993); Aragao, *Theor. Appl. Genet.*, 93:142-150 (1996); *Kim, J., Minamikawa, T., Plant Sci.*, 117:131-138 (1996); Sanford, et al., *Part. Sci. Technol.*, 5:27 (1987); *Sanford, J. C., Trends Biotech.*, 6:299 (1988); Klein, et al., *Bio/technology*, 6:559-563 (1988); *Sanford, J. C., Physiol. Plant*, 7:206 (1990); Klein, et al., *Bio/technology*, 10:268 (1992).

Another method for physical delivery of DNA to plants is sonication of target cells. Zhang, et al., *Bio/technology*, 9:996 (1991). Alternatively, liposome and spheroplast fusion have been used to introduce expression vectors into plants. Deshayes, et al., *EMBO J.*, 4:2731 (1985) and Christou, et al., *PNAS*, 84:3962 (1987). Direct uptake of DNA into protoplasts using $CaCl_2$) precipitation, polyvinyl alcohol, or poly-L-ornithine has also been reported. Hain, et al., *Mol. Gen. Genet.*, 199:161 (1985) and Draper, et al., *Plant Cell Physiol.*, 23:451 (1982). Electroporation of protoplasts and whole cells and tissues for DNA uptake have also been described. Saker, M., Kuhne, T., *Biologia Plantarum*, 40 (4): 507-514 (1997/98); Donn, et al., In Abstracts of VIIth International Congress on Plant Cell and Tissue Culture IAPTC, A2-38, p. 53 (1990); D'Halluin, et al., *Plant Cell*, 4:1495-1505 (1992); and Spencer, et al., *Plant Mol. Biol.*, 24:51-61 (1994). See also Chupean, et al., *Bio/technology*, 7:5, 503-508 (1989).

Following transformation of soybean target tissues, expression of selectable marker genes, e.g., as described above, allows for preferential selection of transformed cells, tissues and/or plants, using regeneration and selection methods now well known in the art.

The foregoing methods for transformation would typically be used for producing a transgenic line. The transgenic line could then be crossed with another (non-transformed or transformed) line in order to produce a new transgenic soybean line. Alternatively, a genetic trait which has been engineered into a particular soybean variety using the foregoing transformation techniques could be introduced into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

Gene Conversions

When the term "soybean plant" is used in the context of the present invention, this also includes any gene conversions of that variety. The term "gene converted plant" as used herein refers to those soybean plants which are developed by backcrossing, genetic engineering, or mutation, where essentially all of the desired morphological and physiological characteristics of a variety are recovered in addition to the one or more genes transferred into the variety via the backcrossing technique, genetic engineering, or mutation.

Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental soybean plant which contributes the gene for the desired characteristic is termed the "nonrecurrent" or "donor parent." This terminology refers to the fact that the nonrecurrent parent is used one time in the backcross protocol and therefore does not recur. The parental soybean plant to which the gene or genes from the nonrecurrent parent are transferred is known as the recurrent parent as it is used for several rounds in the backcrossing protocol. Poehlman & Sleper (1994) and Fehr (1993). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a soybean plant is obtained where essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent variety is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected in the development of a new line but that can be improved by backcrossing techniques. Gene traits may or may not be transgenic. Examples of these traits include, but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. Several of these gene traits are described in U.S. Pat. Nos. 5,777,196, 5,948, 957, and 5,969,212, the disclosures of which are specifically hereby incorporated by reference.

Tissue Culture

Further reproduction of a variety can occur by tissue culture and regeneration. Tissue culture of various tissues of soybean and regeneration of plants therefrom is well known and widely published. For example, reference may be had to Teng, et al., HortScience, 27:9, 1030-1032 (1992); Teng, et al., HortScience, 28:6, 669-1671 (1993); Zhang, et al., Journal of Genetics and Breeding, 46:3, 287-290 (1992); Webb, et al., Plant Cell Tissue and Organ Culture, 38:1, 77-79 (1994); Curtis, et al., Journal of Experimental Botany, 45:279, 1441-1449 (1994); Nagata, et al., Journal for the American Society for Horticultural Science, 125:6, 669-672 (2000); and Ibrahim, et al., Plant Cell Tissue and Organ Culture, 28(2), 139-145 (1992). It is clear from the literature that the state of the art is such that these methods of obtaining plants are routinely used and have a very high rate of success. Thus, another aspect of this invention is to provide cells, which upon growth and differentiation, produce soybean plants having the physiological and morphological characteristics of variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485'.

As used herein, the term "tissue culture" indicates a composition containing isolated cells of the same or a different type, or a collection of such cells organized into parts of a plant. Exemplary plant cells that can generate tissue culture may be derived from parts of plants, such as leaves, pollen, embryos, roots, root tips, anthers, pistils, flowers, seeds, petioles, and the like. Additional compositions that may be used to regenerate plants are protoplasts, calli, and meristematic cells. Means for preparing and maintaining plant tissue cultures are well known in the art. By way of example, tissue cultures containing plant organs have been used to produce regenerated plants. U.S. Pat. Nos. 5,959,185, 5,973,234, and 5,977,445 describe certain techniques, the disclosures of which are incorporated herein by reference.

In some embodiments, a tissue or cell culture of the disclosure is produced from protoplasts or cells from a plant part (e.g., any of a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof). In some embodiments, the cells or protoplasts are produced from a root, root tip, meristematic cell, stem, hypocotyl, petiole, cotyledon, leaf, flower, anther, pollen, pistil, embryo or seed. In some embodiments, the cells or protoplasts are produced from a seed or a portion thereof. In some embodiments, the cells or protoplasts are produced from a fruit or a portion thereof.

Transformation of plant protoplasts can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994) and Ellul et al. (2003). Direct uptake of DNA into protoplasts using CaCl$_2$) precipitation, polyvinyl alcohol, or poly-L-ornithine has also been reported (see, e.g., Hain et al., 1985 and Draper et al., 1982). Electroporation of protoplasts and whole cells and tissues have also been described (see, e.g., Saker et al., 1998; Donn et al., 1990; D'Halluin et al., 1992; and Laursen et al., 1994; Chupean et al., 1989).

Additional Breeding Methods

The present invention is also directed to methods for producing a soybean plant by crossing a first parent soybean plant with a second parent soybean plant where the first or second parent soybean plant is a soybean plant of variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485'. Further, both first and second parent soybean plants can come from soybean variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485'. Thus, any such methods using soybean variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485', are part of the invention, including: selfing, backcrosses, hybrid production, crosses to populations, and the like. All plants produced using soybean variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485', as at least one parent are within the scope of this invention, including those developed from varieties derived from soybean variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485'.

Advantageously, soybean varieties of the disclosure could be used in crosses with other, different, soybean plants to produce first generation (F$_1$) soybean hybrid seeds and plants with superior characteristics. The varieties of the invention can also be used for transformation where exogenous genes are introduced and expressed by the varieties of the invention. Genetic variants created either through traditional breeding methods using soybean variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485', or through transformation of variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485', by any of a number of protocols known to those of skill in the art are intended to be within the scope of this invention.

The following describes breeding methods that may be used with soybean variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485' in the development of further soybean plants. One such embodiment is a method for developing variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485', progeny soybean plants in a soybean plant breeding program, by: obtaining the soybean plant, or a part thereof, of variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485', utilizing said plant or plant part as a source of breeding material, and selecting a soybean variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485', progeny plant with molecular markers in common with variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485' and/or with morphological and/or physiological characteristics selected from the characteristics listed in the section entitled "Objective description of the variety '10020720647'", "Objective description of the variety '10020889109'", "Objective description of the variety '10020889166'", "Objective description of the variety '70020032728'", "Objective description of the variety '70020032975'", "Objective description of the variety '70020033154'", "Objective description of the variety '20598563'", "Objective description of the variety '21097024'", "Objective description of the variety '10021387700'", "Objective description of the variety '10021389471'", "Objective description of the variety '10021384531'", "Objective description of the variety '10021387127'", "Objective description of the variety '10020865219'", "Objective description of the variety '10021384221'", "Objective description of the variety '21097118'", "Objective description of the variety '10021389525'", or "Objective description of the variety '10021384485'". Breeding steps that may be used in the soybean plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of soybean variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485' progeny soybean plants, by crossing variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485' with another soybean plant, thereby producing a population of soybean plants, which, on average, derive 50% of their alleles from soybean variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485'. A plant of this population may be selected and repeatedly selfed or sibbed with a soybean variety resulting from these successive filial generations. One embodiment of this invention is the soybean variety produced by this method and that has obtained at least 50% of its alleles from soybean variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485'. One of ordinary skill in the art of plant breeding would know how to evaluate the traits of two plant varieties to determine if there is no significant difference between the two traits expressed by those varieties. For example, see Fehr and Walt, *Principles of Variety Development*, pp. 261-286 (1987). Thus the invention includes soybean variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485' progeny soybean plants containing a combination of at least two variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485', traits selected from those listed in the section entitled "Objective description of the variety '10020720647'", "Objective description of the variety '10020889109'", "Objective description of the variety '10020889166'", "Objective description of the variety '70020032728'", "Objective description of the variety '70020032975'", "Objective description of the variety '70020033154'", "Objective description of the variety '20598563'", "Objective description of the variety '21097024'", "Objective description of the variety '10021387700'", "Objective description of the variety '10021389471'", "Objective description of the variety '10021384531'", "Objective description of the variety '10021387127'", "Objective description of the variety '10020865219'", "Objective description of the variety '10021384221'", "Objective description of the variety '21097118'", "Objective description of the variety '10021389525'", or "Objective description of the variety '10021384485'", so that said progeny soybean plant is not significantly different for said traits than soybean variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485', as determined at the 5% significance level when grown in the same environmental conditions. Using techniques described herein, molecular markers may be used to identify said progeny plant as a soybean variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485', progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of soybean variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485', may also be characterized through their filial relationship with soybean variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485', as for example, being within a certain number of breeding crosses of soybean variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485'. A breeding cross is a cross made to introduce new genetics into the progeny, and is distinguished from a cross, such as a self or a sib cross, made to select among existing genetic alleles. The lower the number of breeding crosses in the pedigree, the closer the relationship between soybean variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485', and its progeny. For example, progeny produced by the methods described herein may be within 1, 2, 3, 4, or 5 breeding crosses of soybean variety '10020720647', '10020889109', '10020889166', '70020032728', '70020032975', '70020033154', '20598563', '21097024', '10021387700', '10021389471', '10021384531', '10021387127', '10020865219', '10021384221', '21097118', '10021389525', or '10021384485'.

As used herein, the term "plant" includes plant cells, plant protoplasts, plant cell tissue cultures from which soybean plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, and the like.

The use of the terms "a." "an," and "the," and similar referents in the context of describing the invention (especially in the context of the following claims) are to be construed to cover both the singular and the plural, unless otherwise indicated herein or clearly contradicted by context. The terms "comprising," "having." "including." and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

Soybean Variety '10020889166'

A deposit of at least 625 seeds of the soybean variety '10020889166' was made with the American Type Culture Collection (ATCC), ATCC Patent Depository, 10801 University Boulevard, Manassas, Virginia, 20110, USA, and assigned ATCC number PTA-127941. The seeds deposited with the ATCC Patent Depository on Sep. 23, 2025, were obtained from the seed of the variety maintained by GDM Argentina S. A., having an address at Ruta 7 Km 208, Chacabuco, Provincia de Buenos Aires, Argentina, since prior to the filing date of the application. Access to this deposit will be available during the pendency of this application to persons determined by the Commissioner of Patents and Trademarks to be entitled thereto under 37 C.F.R. § 1.14 and 35 U.S.C. § 122. Upon issuance, the Applicant will make the deposit available to the public consistent with all of the requirements of 37 C.F.R. § 1.801-1.809. This deposit of the soybean variety '10020889166' will be maintained in the ATCC Patent Depository, which is a public depository, for a period of 30 years, or at least 5 years after the most recent request for a sample of the deposit, or for the effective life of the patent, whichever is longer, and will be replaced if it becomes nonviable during that period. Applicant has no authority to waive any restrictions imposed by law on the transfer of biological material or its transportation in commerce. Applicant does not waive any infringement of rights granted under this patent or under the Plant Variety Protection Act (7 USC 2321 et seq.).

What is claimed is:

1. A soybean seed designated as '10020889166', representative sample of seed having been deposited under ATCC Accession Number PTA-127941.

2. A soybean plant produced by growing the seed of claim 1.

3. A plant part from the plant of claim 2.

4. The plant part of claim 3, wherein said part is a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof.

5. The plant part of claim 4, wherein said part is a pod.

6. A soybean plant having all the physiological and morphological characteristics of the soybean plant of claim 2.

7. A plant part from the plant of claim 6.

8. The plant part of claim 7, wherein said part is a pollen grain, ovule, protoplast, cell, embryo, cotyledon, hypocotyl, meristem, root, pistil, anther, flower, stem, pod, leaf, petiole, callus, rootstock, scion, cutting, stem, ovary, pericarp, embryo sac, microspore, or a portion thereof.

9. The plant part of claim 8, wherein said part is a pod.

10. An $F_1$ hybrid soybean plant having '10020889166' as a parent wherein '10020889166' is grown from the seed of claim 1.

11. A pollen grain or an ovule of the plant of claim 2.

12. A tissue culture of the plant of claim 2.

13. A soybean plant regenerated from the tissue culture of claim 12, wherein the plant has all of the morphological and physiological characteristics of a soybean plant produced by growing seed designated as '10020889166' having ATCC Accession Number PTA-127941.

14. A method of making soybean seeds, said method comprising crossing the plant of claim 2 with another soybean plant and harvesting seed therefrom.

15. A method of producing a commodity plant product, said method comprising obtaining the plant of claim 2 or a part thereof and producing said commodity plant product therefrom.

16. The method of claim 15, wherein the commodity plant product is protein concentrate, protein isolate, hulls, meal, flour, or oil.

17. A method of making a soybean variety designated as '10020889166', said method comprising selecting seeds from the cross of one '10020889166' plant with another '10020889166' plant, a sample of '10020889166' soybean seed having been deposited under ATCC Accession Number PTA-127941.

\* \* \* \* \*